(12) United States Patent
Coppens et al.

(10) Patent No.: US 9,192,534 B2
(45) Date of Patent: Nov. 24, 2015

(54) MODULAR PATIENT TRANSPORT SYSTEM

(71) Applicant: Qfix Systems, LLC, Avondale, PA (US)

(72) Inventors: Daniel D. Coppens, Avondale, PA (US); Richard J. Herrschaft, Wester Chester, PA (US); Zachary E. Knezo, Coatesville, PA (US); John R. Capone, West Chester, PA (US); David M. Rabeno, Avondale, PA (US)

(73) Assignee: Qfix Systems, LLC, Avondale, PA (US)

( * ) Notice: Subject to any disclaimer, the term of this patent is extended or adjusted under 35 U.S.C. 154(b) by 114 days.

(21) Appl. No.: 14/044,395

(22) Filed: Oct. 2, 2013

(65) Prior Publication Data

US 2014/0090168 A1    Apr. 3, 2014

Related U.S. Application Data

(60) Provisional application No. 61/709,098, filed on Oct. 2, 2012.

(51) Int. Cl.
*A61G 7/10* (2006.01)
*A61G 7/14* (2006.01)
(Continued)

(52) U.S. Cl.
CPC ............ *A61G 7/1025* (2013.01); *A61B 6/0407* (2013.01); *A61G 7/103* (2013.01); *A61G 7/012* (2013.01); *A61G 13/1225* (2013.01); *A61G 2007/0528* (2013.01); *A61G 2210/50* (2013.01)

(58) Field of Classification Search
CPC .................................... A61G 7/10; A61G 7/14
USPC ........... 5/81.1 R, 81.1 HS, 81.1 RP, 601, 86.1
See application file for complete search history.

(56) References Cited

U.S. PATENT DOCUMENTS

| 4,259,756 A | 4/1981 | Pace |
| 6,584,626 B1 | 7/2003 | DiRoma |

(Continued)

FOREIGN PATENT DOCUMENTS

| JP | 2002082975 A | 3/2002 |
| KR | 100896817 B1 | 5/2009 |

(Continued)

OTHER PUBLICATIONS

International Search Report for PCT/US2013/63080; Filing Date Oct. 23, 2013.

*Primary Examiner* — Fredrick Conley
(74) *Attorney, Agent, or Firm* — RatnerPrestia

(57) ABSTRACT

Advantageous patient transport systems, and related methods of use, are provided. More particularly, the present disclosure provides advantageous modular patient transport systems that are configured to transport patients from one surface to another for various applications (e.g., diagnostic imaging and/or radiation therapy applications). The patient transport systems/assemblies of the present disclosure are configured and dimensioned to be utilized with a wide variety of imaging and/or treatment modalities/environments. The target modality assemblies/surfaces that the patient may be transported to and/or from via the improved patient transport systems/assemblies of the present disclosure include many different types of equipment/surfaces. In certain embodiments, when the transfer assembly is moved to the target modality assembly, a safety member of the transfer assembly engages with a safety member catch of the target modality assembly to allow a user to safely, accurately and repeatably releasably mount the transfer assembly to the target modality assembly.

21 Claims, 30 Drawing Sheets

(51) Int. Cl.
  *A61B 6/04* (2006.01)
  *A61G 7/012* (2006.01)
  *A61G 13/12* (2006.01)
  *A61G 7/05* (2006.01)

(56) References Cited

U.S. PATENT DOCUMENTS

| | | |
|---|---|---|
| 6,701,544 B2 | 3/2004 | Heimbrock |
| 6,718,571 B2 | 4/2004 | Bartels |
| 7,191,854 B2 | 3/2007 | Lenkman |
| 7,228,579 B2 | 6/2007 | Tidwell |
| 7,337,477 B2 | 3/2008 | Scordato et al. |
| 8,171,580 B2 | 5/2012 | Wilson et al. |
| 8,234,727 B2 | 8/2012 | Schreiber et al. |
| 8,490,226 B2 | 7/2013 | Koger et al. |
| 2002/0095722 A1* | 7/2002 | Korver et al. .......... 5/81.1 R |
| 2006/0174405 A1* | 8/2006 | Johnson ................. 5/81.1 R |
| 2007/0074347 A1 | 4/2007 | Coppens et al. |
| 2012/0043475 A1 | 2/2012 | Ahn |
| 2013/0212806 A1 | 8/2013 | Coppens et al. |

FOREIGN PATENT DOCUMENTS

| | | |
|---|---|---|
| WO | WO-2009131818 A2 | 10/2009 |
| WO | WO-2011139062 A2 | 11/2011 |

\* cited by examiner

MODULAR PATIENT TRANSPORT SYSTEM

CROSS-REFERENCE TO RELATED APPLICATIONS

This application claims the benefit of U.S. Provisional Application No. 61/709,098 filed Oct. 2, 2012, all of which is herein incorporated by reference in its entirety.

BACKGROUND

1. Technical Field

The present disclosure relates to patient transport systems and related methods of use and, more particularly, to modular patient transport systems that are configured to transport patients from one surface to another for various applications (e.g., for diagnostic imaging and/or radiation therapy applications).

2. Background Art

In general, patient transport systems or the like are known. For example, it is sometimes desirable/necessary to transport a patient from one assembly/surface to another (e.g., from one target modality assembly or treatment assembly to another). Some exemplary patient transport systems and related systems/accessories or the like are described and disclosed in U.S. Pat. Nos. 8,490,226; 8,234,727; 8,171,580; 7,228,579; 7,191,854; 6,701,544; 6,718,571; 6,584,626 and 4,259,756, and U.S. Patent Pubs. Nos. 2013/0212806 and 2007/0074347, and U.S. Patent Application Ser. Nos. 61/836,707 and 61/865,539, and WO2011/139062; JP02082975 and KR896817, the entire contents of each being hereby incorporated by reference in their entireties.

A constant need exists among patient transport system manufacturers to develop patient transport systems and related systems/accessories that are cost-effective and/or include improved features/structures.

For example, some equipment used today for diagnostic imaging and cancer treatment is sophisticated and expensive. To attempt to maximize the utilization of this equipment it is desirable to be able to transport a patient to and from the equipment on a transport system/assembly which allows rapid change over from one patient to the next.

Moreover, some procedures require a rapid transition from one type of equipment to the next. As such, there are instances in which a patient is taken from one imaging modality (e.g., CT, PET/CT, MRI, etc.) to another, or from an imaging modality to the treatment room in succession. For example, it is often desirable to perform positron emission tomography/computed tomography ("PET/CT") and magnetic resonance imaging ("MRI") exams in close time proximity so that the biological effect of interest can be seen in both machines. An effective patient transport system can be a significant aid in such situations.

Radiation therapy and diagnostic imaging equipment are often used in hospitals and treatment centers. Some techniques for radiation therapy and diagnostic imaging require that patients be positioned and immobilized precisely. Generally, treatment of a tumor by radiation therapy is preceded by a diagnostic imaging procedure called simulation. During simulation, the patient is positioned in the manner anticipated for treatment. This can include the physical orientation of the patient using the positioning and immobilization assemblies/devices that will be used in treatment.

Furthermore, some state of the art cancer radiation therapy is increasingly based on the pinpoint application of high-energy radiation, which can be highly tailored to the shape and position of the cancerous tumor. As the size of the treatment beam decreases, the accurate location of the beam becomes much more critical. For example, if a highly tailored treatment beam is off target (e.g., by a few millimeters), it may miss the tumor. Because of these new techniques, it becomes increasingly desirable to know the location/shape of the tumor accurately when the patient is positioned for treatment.

Thus, an interest exists for improved patient transport systems and related assemblies/accessories. These and other inefficiencies and opportunities for improvement are addressed and/or overcome by the assemblies, systems and methods of the present disclosure.

SUMMARY

The present disclosure provides advantageous patient transport systems, and related methods of use. More particularly, the present disclosure provides advantageous modular patient transport systems that are configured to transport patients from one surface to another for various applications/treatments (e.g., for diagnostic imaging and/or high-energy radiation therapy applications/environments).

In exemplary embodiments, the patient transport systems/assemblies of the present disclosure are configured and dimensioned to be utilized with a wide variety of imaging and/or treatment modalities/environments. For example, the target treatment assemblies/surfaces that the patient may be transported to and/or from (via the improved patient transport assemblies/systems of the present disclosure) can include many different types of equipment/surfaces (e.g., radiation therapy treatment, CT, MRI and/or brachytherapy equipment/tables/surfaces, etc.).

In certain embodiments, the present disclosure provides for a patient transport system that allows a patient to be positioned and/or immobilized on a supporting/transfer assembly (e.g., transfer surface), and then transferred onto the surface of a target modality assembly (e.g., treatment assembly) for various applications and/or treatments. The supporting/transfer assembly can be compatible with a variety of diagnostic imaging, radiation therapy applications and/or treatment modalities or the like.

In exemplary embodiments, when the transfer assembly is releasably engaged with the target modality assembly, the transfer assembly is prevented from moving laterally relative to the target modality assembly, thereby providing a highly advantageous safety feature (e.g., the transfer assembly will not slide off the opposite lateral side of the target modality assembly when loading the transfer assembly, etc.). Likewise, when the exemplary transfer assembly is releasably engaged with the trolley assembly, the transfer assembly is prevented from moving laterally relative to the trolley assembly, thereby providing a highly advantageous safety feature (e.g., the transfer assembly will not slide off the opposite lateral side of the trolley assembly when loading the transfer assembly, etc.).

Moreover, the advantageous trolley assemblies, target modality assemblies and transfer assemblies of the present disclosure provide improved features/structures that allow the transfer assembly to be accurately and repeatably loaded/positioned on the trolley assembly or the target modality assembly at the same locations/positions after every transfer assembly loading process.

The present disclosure provides for a patient transport system including a target modality assembly; a patient transfer assembly, the transfer assembly configured and dimensioned to be releasably mounted with respect to the target modality assembly; wherein when the transfer assembly is moved to the target modality assembly, the transfer assembly is moved to a predetermined stop position on the target modality assembly to allow a user to safely, accurately and repeatably releasably mount the transfer assembly to the target modality assembly.

The present disclosure also provides for a patient transport system wherein the target modality assembly includes a safety member catch; and wherein when the transfer assembly is moved to the target modality assembly, a safety member of the transfer assembly engages with the safety member catch of the target modality assembly to allow a user to safely, accurately and repeatably releasably mount the transfer assembly to the target modality assembly.

The present disclosure also provides for a patient transport system wherein when the safety member is engaged with the safety member catch of the target modality assembly and the safety member catch is in a safety position, the transfer assembly is prevented from moving laterally relative to the target modality assembly.

The present disclosure also provides for a patient transport system further including a trolley assembly, the trolley assembly having a safety member catch; wherein the transfer assembly is configured and dimensioned to be releasably mounted with respect to the trolley assembly; and wherein when the transfer assembly is moved from the target modality assembly to the trolley assembly, a safety member of the transfer assembly engages with the safety member catch of the trolley assembly to allow a user to safely, accurately and repeatably releasably mount the transfer assembly to the trolley assembly.

The present disclosure also provides for a patient transport system wherein when the safety member is engaged with the safety member catch of the trolley assembly and the safety member catch is in a safety position, the transfer assembly is prevented from moving laterally relative to the trolley assembly.

The present disclosure also provides for a patient transport system wherein the transfer assembly is configured to be laterally moved from either lateral side of the target modality assembly across either lateral side of the trolley assembly to a predetermined stop position on the trolley assembly to releasably mount the transfer assembly to the trolley assembly.

The present disclosure also provides for a patient transport system wherein the target modality assembly further includes a locking member and the transfer assembly includes a locating member; wherein when the transfer assembly is moved to the target modality assembly, the locating member engages with the locking member and allows a user to accurately and repeatably locate and rigidly lock in one location the transfer assembly to the target modality assembly in a releasable manner; wherein a top side of the target modality assembly includes a groove; wherein the transfer assembly includes an extending member, the extending member extending from a bottom side of the transfer assembly; wherein at least a portion of the extending member is positioned within the groove when the transfer assembly is releasably mounted to the target modality assembly; and wherein when the transfer assembly is releasably locked to the target modality assembly, the locking member urges the extending member into releasable locking contact with a wall of the groove to rigidly lock the transfer assembly to the target modality assembly in a releasable manner.

The present disclosure also provides for a patient transport system wherein the locating member and locking member are configured to allow the user to accurately and repeatably locate and rigidly lock in one location the transfer assembly to the target modality assembly to the level of sub-millimeter accuracy.

The present disclosure also provides for a patient transport system wherein when the transfer assembly is releasably mounted to the target modality assembly, the safety member catch and the safety member are positioned outside of the treatment or imaging area of the target modality assembly.

The present disclosure also provides for a patient transport system wherein the safety member catch of the target modality assembly is defined by a first safety latching member and a second safety latching member when the first and second safety latching members are in a safety position; wherein a top side of the target modality assembly includes a first groove; and wherein at least a portion of the first and second safety latching members are positioned within the first groove when the first and second safety latching members are in the safety position; wherein the top side of the target modality assembly includes a second groove; wherein the transfer assembly includes a guide member, the guide member extending from a bottom side of the transfer assembly; wherein at least a portion of the guide member is positioned within the second groove when the transfer assembly is releasably mounted to the target modality assembly; and wherein the guide member is configured and dimensioned to engage the second groove and prevent the transfer assembly from being lifted vertically or upwardsly off of the target modality assembly when the transfer assembly is releasably mounted to the target modality assembly.

The present disclosure also provides for a patient transport system wherein a top side of the target modality assembly includes an extending member, the extending member extending from the top side of the target modality assembly; wherein a bottom side of the transfer assembly includes a groove; and wherein at least a portion of the extending member is positioned within the groove when the transfer assembly is releasably mounted to the target modality assembly.

The present disclosure also provides for a patient transport system including a target modality assembly, the target modality assembly having an interlock member; a trolley assembly, the trolley assembly having an interlock member; a patient transfer assembly, the transfer assembly configured and dimensioned to be releasably mounted with respect to the trolley assembly or to the target modality assembly; wherein when the transfer assembly is releasably mounted with respect to the trolley assembly, the engagement of the interlock member of the trolley assembly with the target modality assembly allows the transfer assembly to be released from the trolley assembly and moved to the target modality assembly.

The present disclosure also provides for a patient transport system wherein the transfer assembly is configured to be laterally moved from either lateral side of the trolley assembly across either lateral side of the target modality assembly to a predetermined stop position on the target modality assembly to releasably mount the transfer assembly to the target modality assembly.

The present disclosure also provides for a patient transport system wherein when the transfer assembly is releasably mounted with respect to the target modality assembly, the engagement of the interlock member of the target modality assembly with the trolley assembly allows the transfer assembly to be released from the target modality assembly and moved to the trolley assembly.

The present disclosure also provides for a patient transport system wherein the transfer assembly is configured to be laterally moved from either lateral side of the target modality assembly across either lateral side of the trolley assembly to a predetermined stop position on the trolley assembly to releasably mount the transfer assembly to the trolley assembly.

The present disclosure also provides for a patient transport system wherein the target modality assembly includes a safety member catch and the trolley assembly includes a safety member catch; and wherein when the transfer assembly is moved to the target modality assembly, a safety member of the transfer assembly engages with the safety member catch of the target modality assembly to allow a user to safely, accurately and repeatably releasably mount the transfer assembly to the target modality assembly; wherein when the transfer assembly is releasably mounted with respect to the target modality assembly, the engagement of the interlock member of the target modality assembly with the trolley assembly allows the transfer assembly to be released from the target modality assembly and moved to the trolley assembly; and wherein when the transfer assembly is moved from the target modality assembly to the trolley assembly, the safety member of the transfer assembly engages with the safety member catch of the trolley assembly to allow a user to safely, accurately and repeatably releasably mount the transfer assembly to the trolley assembly.

The present disclosure also provides for a patient transport system wherein when the safety member is engaged with the safety member catch of the target modality assembly and the safety member catch is in a safety position, the transfer assembly is prevented from moving laterally relative to the target modality assembly; and wherein when the safety member is engaged with the safety member catch of the trolley assembly and the safety member catch is in a safety position, the transfer assembly is prevented from moving laterally relative to the trolley assembly.

The present disclosure also provides for a patient transport system wherein the safety member catch of the target modality assembly is defined by a first safety latching member and a second safety latching member when the first and second safety latching members are in a safety position; wherein a top side of the target modality assembly includes a first groove; and wherein at least a portion of the first and second safety latching members are positioned within the first groove when the first and second safety latching members are in a safety position.

The present disclosure also provides for a patient transport system wherein when the interlock member of the trolley assembly is engaged with the target modality assembly, the engaged interlock member moves an interlock transfer member to a position to allow a release cable pull member to rotate when a safety latch release pull trigger is utilized by a user, which thereby pulls a cable connected to the first safety latching member and puts the first safety latching member into a released position that allows the transfer assembly to be moved to the target modality assembly; and wherein when the transfer assembly is moved to the target modality assembly, the safety member of the transfer assembly is configured to depress a safety latch reset member of the first safety latching member, which thereby resets the first safety latching member to the safety position after the transfer assembly is moved to the target modality assembly.

The present disclosure also provides for a patient transport system wherein the top side of the target modality assembly includes a second groove; wherein the transfer assembly includes a guide member, the guide member extending from a bottom side of the transfer assembly; wherein at least a portion of the guide member is positioned within the second groove when the transfer assembly is releasably mounted to the target modality assembly; and wherein the guide member is configured and dimensioned to engage the second groove and prevent the transfer assembly from being lifted vertically or upwardsly off of the target modality assembly when the transfer assembly is releasably mounted to the target modality assembly.

The present disclosure also provides for a patient transport system wherein the target modality assembly further includes a locking member and the transfer assembly includes a locating member; wherein when the transfer assembly is moved to the target modality assembly, the locating member engages with the locking member and allows a user to accurately and repeatably locate and rigidly lock in one location the transfer assembly to the target modality assembly in a releasable manner; wherein a top side of the target modality assembly includes a groove; wherein the transfer assembly includes an extending member, the extending member extending from a bottom side of the transfer assembly; wherein at least a portion of the extending member is positioned within the groove when the transfer assembly is releasably mounted to the target modality assembly; and wherein when the transfer assembly is releasably locked to the target modality assembly, the locking member urges the extending member into releasable locking contact with a wall of the groove to rigidly lock the transfer assembly to the target modality assembly in a releasable manner.

The present disclosure also provides for a patient transport system wherein the locating member and locking member are configured to allow the user to accurately and repeatably locate and rigidly lock in one location the transfer assembly to the target modality assembly to the level of sub-millimeter accuracy.

The present disclosure also provides for a patient transport system wherein a top side of the target modality assembly includes an extending member, the extending member extending from the top side of the target modality assembly; wherein a bottom side of the transfer assembly includes a groove; and wherein at least a portion of the extending member is positioned within the groove when the transfer assembly is releasably mounted to the target modality assembly.

The present disclosure also provides for a patient transport system wherein at least a portion of the transfer assembly and at least a portion of the target modality assembly is at least one of x-ray translucent and MRI compatible. The present disclosure also provides for a patient transport system wherein the target modality assembly is configured and dimensioned to be utilized in connection with an imaging or treatment assembly.

The present disclosure also provides for a method for transporting a patient including providing a target modality assembly, the target modality assembly having a safety member catch; providing a patient transfer assembly; and moving the patient transfer assembly to the target modality assembly to cause a safety member of the patient transfer assembly to engage with the safety member catch of the target modality assembly to safely, accurately and repeatably releasably mount the patient transfer assembly to the target modality assembly.

The present disclosure also provides for a method for transporting a patient including providing a target modality assembly, the target modality assembly having an interlock member; providing a trolley assembly, the trolley assembly having an interlock member; providing a patient transfer assembly, the transfer assembly configured and dimensioned to be releasably mounted with respect to the trolley assembly or to the target modality assembly; releasably mounting the transfer assembly to the trolley assembly; engaging the interlock member of the trolley assembly with the target modality assembly to release the transfer assembly from the trolley assembly; and moving the released transfer assembly to the target modality assembly.

Any combination or permutation of embodiments is envisioned. Additional advantageous features, functions and applications of the disclosed assemblies, systems and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the spirit and scope of the present disclosure. To assist those of ordinary skill in the art in making and using the disclosed systems, assemblies and methods, reference is made to the appended figures, wherein.

DETAILED DESCRIPTION

Figure 1:
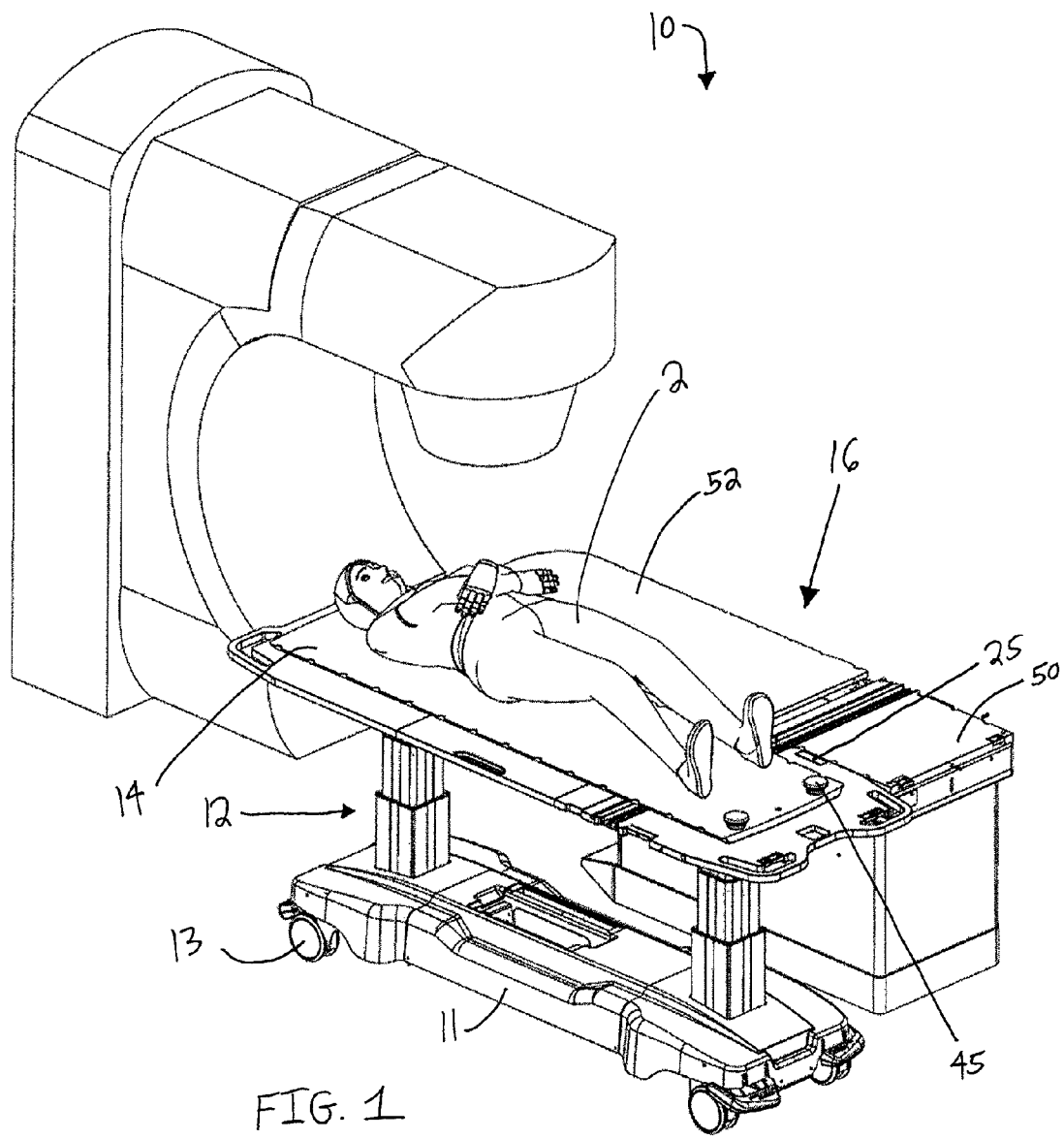
FIGS. 1-2 are side perspective views of an exemplary patient transport system according to the present disclosure.

The exemplary embodiments disclosed herein are illustrative of advantageous patient transport systems, and systems/assemblies of the present disclosure and methods/techniques thereof. It should be understood, however, that the disclosed embodiments are merely exemplary of the present disclosure, which may be embodied in various forms. Therefore, details disclosed herein with reference to exemplary patient transport systems or fabrication methods and associated processes or techniques of assembly and use are not to be interpreted as limiting, but merely as the basis for teaching one skilled in the art how to make and use the advantageous assemblies/systems and/or alternative assemblies/systems of the present disclosure.

The present disclosure provides improved patient transport systems, and related methods of use. More particularly, the present disclosure provides modular patient transport systems that are configured to transport patients from one surface to another for various treatments/applications. For example, patients may be transferred, via the transport systems/assemblies of the present disclosure, from one surface to another for diagnostic imaging (e.g., diagnostic imaging x-ray environments) and/or radiation therapy applications (e.g., photon, proton and/or electron radiation therapy environments), although the present disclosure is not limited thereto. Rather, it is noted that patients may be transferred via the transport systems/assemblies of the present disclosure from one surface to another for a wide variety of purposes/treatments/applications.

In certain embodiments, the patient transport systems of the present disclosure are configured and dimensioned to be utilized with a wide variety of imaging and/or treatment modalities/environments. As such, the target treatment assemblies/surfaces that the patient may be transported to and/or from (via the advantageous patient transport systems/assemblies of the present disclosure) may include many different types of equipment/surfaces (e.g., radiation therapy treatment tables/surfaces, CT tables/surfaces, MRI tables/surfaces, brachytherapy tables/surfaces, etc.).

In exemplary embodiments, the patient transport system allows a patient to be positioned or immobilized on a supporting/transfer assembly (e.g., on a transfer assembly which is positioned on a trolley assembly), and then transferred (e.g., laterally transferred from the trolley assembly) onto the surface of a target modality assembly (e.g., treatment assembly) for various purposes/applications/treatments. In general, the transfer assembly is compatible with a variety of diagnostic imaging, radiation therapy applications and/or treatment modalities or the like. In certain embodiments, it is beneficial to use the same devices/assemblies for radiation treatment and diagnostic imaging. For example, by using the same devices/assemblies, hospitals and treatment centers can have better utilization of equipment and higher patient throughput. This in turn can lower costs and provide faster patient care. This can also ensure that the patient is being treated on the same equipment they were simulated on, which allows for accurate calculations of the attenuation properties of the equipment during treatment planning.

Current practice provides that it is important that the patient be simulated in substantially the same position on the assemblies/devices as will be used in treatment to attempt to ensure accurate tumor location identification for treatment. Accurate tumor location and treatment spares the surrounding healthy tissue. This patient positioning and/or immobilization process can be extensive and time consuming. It can be beneficial, therefore, to set up the patient beforehand outside the room containing the actual treatment or imaging equipment to better utilize time on the treatment or imaging equipment. In some cases, imaging and treatment are done on the same day. In these cases it can be beneficial to set up the patient once and have them remain positioned/immobilized throughout the imaging and/or treatment procedures. When transporting patients from one piece of equipment to another, it is generally desirable to employ an efficient and easy-to-use patient transfer system, as such a system can provide for the safe and efficient transfer of a patient from one target modality/surface to another. It is noted that an easy and safe transfer is beneficial for both the patient and the operator moving the patient.

In exemplary embodiments, the present disclosure provides for improved and easy-to-use patient transport systems/assemblies that are configured to safely transport patients from one surface to another for various applications (e.g., diagnostic imaging and/or radiation therapy applications), thereby providing a significant operational, commercial and/or manufacturing advantage as a result. Moreover, by utilizing the same assemblies/systems of the present disclosure for treatment/applications (e.g., for radiation treatment and/or diagnostic imaging), the users (e.g., hospitals and treatment centers) can experience improved utilization of equipment and higher patient throughput, which in turn can lower costs and provide improved/faster patient care. Furthermore, exemplary patient transport systems/assemblies of the present disclosure provide that the patient can be repeatably positioned and/or immobilized precisely, thereby providing a significant operational, commercial and/or manufacturing advantage as a result.

Furthermore, the patient transport systems/assemblies of the present disclosure can provide for the efficient use of treatment equipment by enabling set-up of the patient on the positioning/immobilization assembly/device in a separate room, thereby leaving the treatment equipment free until needed. It can also provide a means to use the same assembly/device for imaging and radiation therapy. For example, the positioned patient/assembly (e.g., positioned/immobilized patient on a transfer assembly) can be transferred from the set-up table to a transport device/assembly (e.g., trolley assembly), and then the patient/assembly can be moved from the trolley assembly to imaging equipment, then back to the trolley, then onto other target modality equipment (and advantageously only require one patient set-up on the positioning/transfer assembly surface).

Referring now to the drawings, like parts are marked throughout the specification and drawings with the same reference numerals, respectively. Drawing figures are not necessarily to scale and in certain views, parts may have been exaggerated for purposes of clarity.

Figure 2:
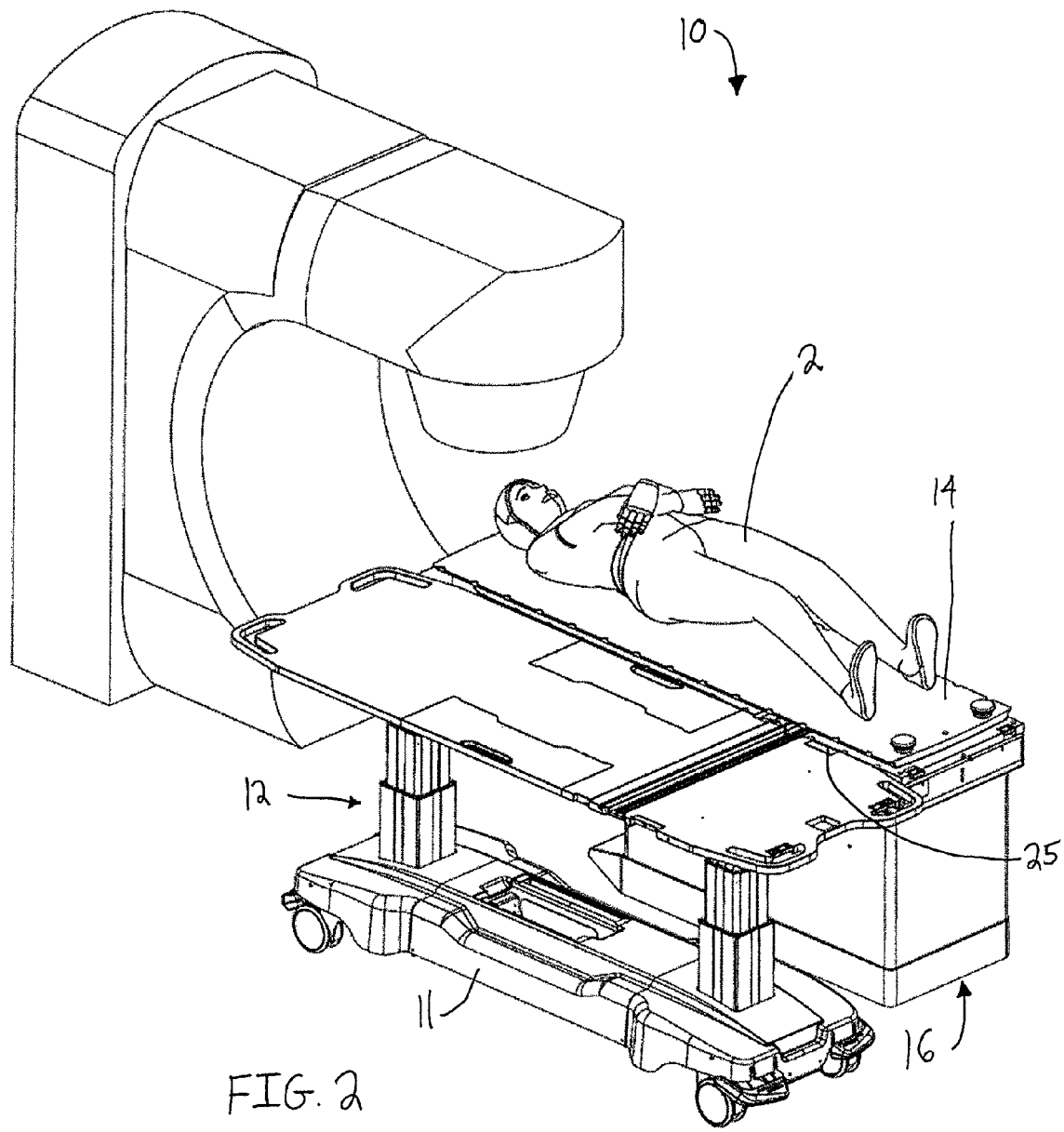

With reference to FIGS. 1-2, there is illustrated an embodiment of an exemplary patient transport system 10 according to the present disclosure. In general, patient transport system 10 is configured and dimensioned for patient transporting and/or treatment purposes. As discussed in further detail below, it is noted that patient transport system 10 can take a variety of forms and/or designs.

As shown in FIGS. 1-2, exemplary patient transport system 10 includes a trolley assembly 12, a transfer assembly 14 and a target modality assembly 16. In general, patient transport system 10 is a modular patient transport system that is configured to transport patients 2 from one surface to another for various treatments/applications. For example, patients 2 may be transferred, via system 10, from one surface to another for diagnostic imaging and/or radiation therapy applications, although the present disclosure is not limited thereto. Rather, it is noted that patients 2 may be transferred via the assemblies of system 10 from one surface to another for a wide variety of purposes/treatments/applications.

FIGS. 1-2 are side perspective views of an exemplary patient transport system 10 according to the present disclosure. More particularly, patient transport system 10 utilizes trolley assembly 12, transfer assembly 14 and/or target modality assembly 16 for patient transporting and/or treatment (or imaging) purposes. For example, assembly 16 can be a radiation therapy target modality assembly 16, such as, without limitation, a linear accelerator to deliver treatment during photon radiation treatment, although the present disclosure is not limited thereto.

In general, trolley assembly 12 and transfer assembly 14 of patient transport system 10 are configured and dimensioned to be utilized in conjunction with a wide variety of imaging and/or treatment modalities, environments or assemblies 16. For example, the target modality assemblies 16 that the patient 2 may be transported to and/or from (e.g., via the trolley assembly 12 and transfer assembly 14, as discussed below) may include many different types of equipment/surfaces (e.g., radiation therapy treatment tables/surfaces, CT tables/surfaces, MRI tables/surfaces, brachytherapy tables/surfaces, etc.).

As shown in FIGS. 1-2 and as discussed in further detail below, patient transport system 10 allows a patient 2 to be positioned or immobilized on a transfer assembly 14 (e.g., on transfer assembly 14 which is positioned on trolley assembly 12), and then transferred (e.g., laterally transferred from the trolley assembly 12) onto the surface of a target modality assembly 16 for various purposes/applications/treatments. In exemplary embodiments, transfer assembly 14 is compatible with a variety of diagnostic imaging, radiation therapy applications and/or treatment modalities or the like. As noted, it is beneficial to use the same devices/assemblies for radiation treatment and diagnostic imaging. Thus, by advantageously using the same transfer assembly 14 for radiation treatment and diagnostic imaging, users (e.g., hospitals and treatment centers) experience improved utilization of equipment and higher patient 2 throughput, which lowers cost and provides faster patient care. This also ensures that the equipment the patient is treated on has the same attenuation properties as that used during simulation. This allows for the accurate calculation of attenuation during treatment planning.

Moreover, in certain embodiments it is important that the patient 2 be simulated in substantially the same position on the assembly as will be used in treatment to attempt to ensure accurate tumor location identification for treatment, and this patient positioning/immobilization process can be extensive and time consuming. Thus, it is beneficial to set up the patient 2 beforehand on transfer assembly 14 (and other than in the room containing the actual treatment or imaging equipment) to better utilize time on the treatment or imaging equipment. Furthermore, imaging and treatment can be done on the same day, and in these cases it is beneficial to set up the patient 2 once on transfer assembly 14 and have them remain positioned/immobilized throughout the imaging and/or treatment procedures. As such, patient transport system 10 is an improved and easy-to-use patient transport system that is configured to safely transport patients 2 from one surface to another for various applications. It is noted that an easy and safe transfer is beneficial for both the patient 2 and the operator moving the patient 2.

Moreover, by utilizing the same assemblies (e.g., transfer assembly 14) of system 10 for various treatment/applications (e.g., for radiation treatment and/or diagnostic imaging), the users (e.g., hospitals and treatment centers) of system 10 experience improved utilization of equipment and higher patient 2 throughput, as noted. In exemplary embodiments and as discussed further below, the assemblies (e.g., transfer assembly 14 and target modality assembly 16) of system 10 provide that the patient 2 can be repeatably positioned and/or immobilized precisely, thereby providing a significant advantage during utilization of system 10 for treatment purposes or the like.

In certain embodiments, the assemblies of system 10 provide for the efficient use of target modality assembly 16 by enabling set-up of the patient 2 on the positioning, immobilization and/or transferring assemblies (e.g., transfer assembly 14 and/or trolley assembly 12) in a separate room, thereby leaving the target modality assembly 16 free until needed. System 10 can also provide a means to use the same assembly (e.g., transfer assembly 14) for imaging and radiation therapy, as noted. For example, the positioned/immobilized patient 2 on transfer assembly 14 can be positioned on trolley assembly 12, and then the patient 2/assembly 14 can be moved from the trolley assembly 12 to target modality equipment 16, and then back to the trolley assembly 12, then onto other target modality equipment 16 (e.g., radiation therapy equipment) at a different location, while advantageously only requiring one patient 2 set-up on the transfer assembly 14. In exemplary embodiments, at least a portion of the transfer assembly 14 and at least a portion of the target modality assembly 16 is at least one of x-ray translucent and MRI compatible.

With reference to FIGS. 5-12, there is illustrated an embodiment of an exemplary trolley assembly 12 according to the present disclosure. In general, trolley assembly 12 is configured and dimensioned for patient transporting purposes. It is noted that trolley assembly 12 can take a variety of forms and/or designs.

In exemplary embodiments, trolley assembly 12 includes a base member 11 having one or more wheels 13 for patient transporting purposes (e.g., four wheels 13), and one or more columns 15 (e.g., two columns 15) extending from the base member 11 to a supporting frame 17. In general, supporting frame 17 includes a top side 18, bottom side 19, first end 20, second end 21, first side 22 and second side 23. In certain embodiments and as discussed in further detail below, top side 18 of supporting frame 17 defines a substantially planar top side or surface 18 and includes structures/features (e.g., grooves 24, 24') that are configured and dimensioned to releasably mount with respect to a patient transfer assembly 14.

In some embodiments, each wheel 13 can be associated with a brake, and each column 15 is adjustable (e.g., vertically and/or horizontally adjustable). Trolley assembly 12 may or may not include motorized travel means. Exemplary trolley assembly 12 includes one or more user-friendly handles 28 for patient transporting purposes.

Figure 5:
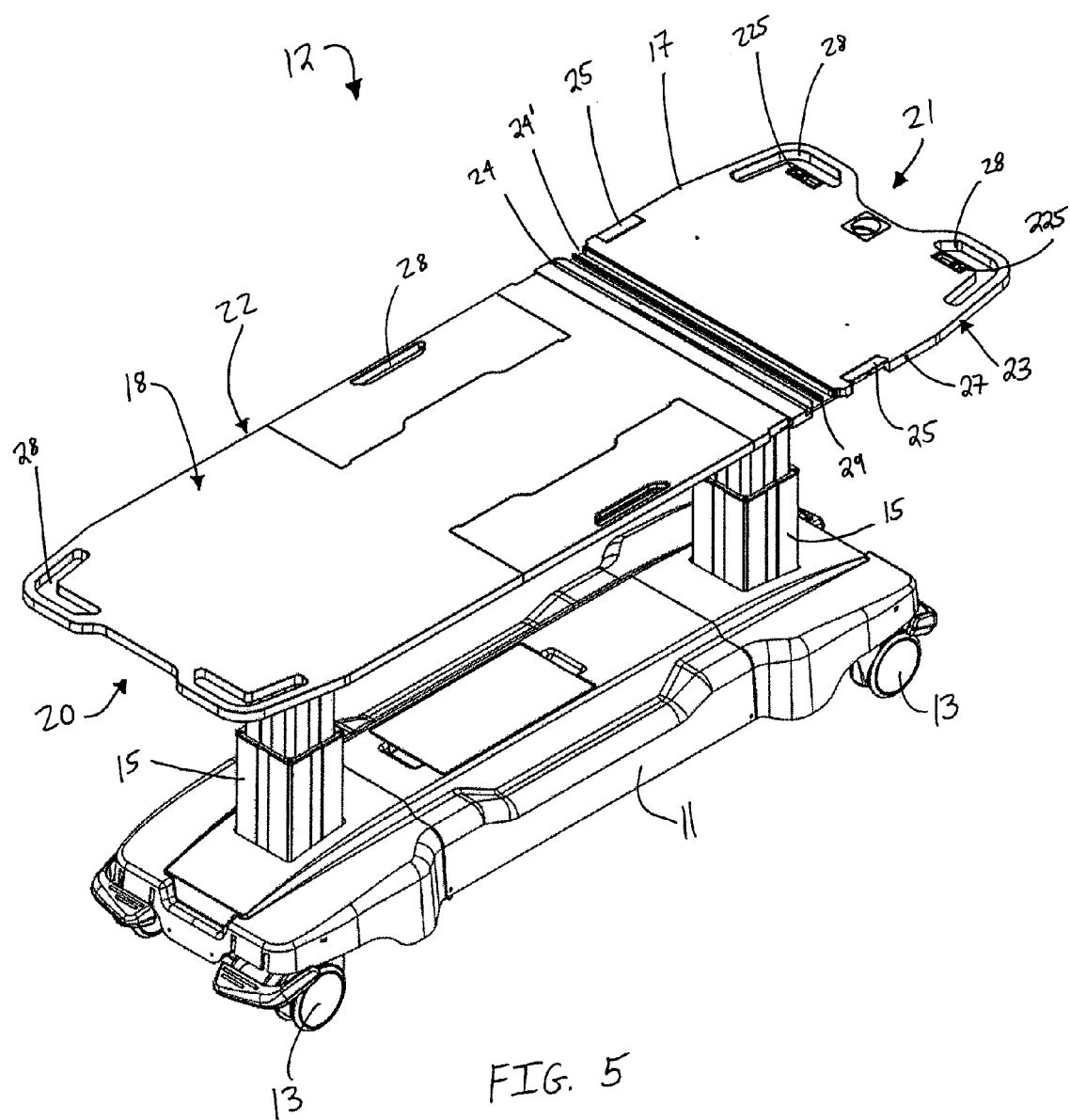
FIG. 5 is a top-side perspective view of an exemplary trolley assembly according to the present disclosure, prior to exemplary transfer assembly being releasably mounted thereon.
Figure 6:
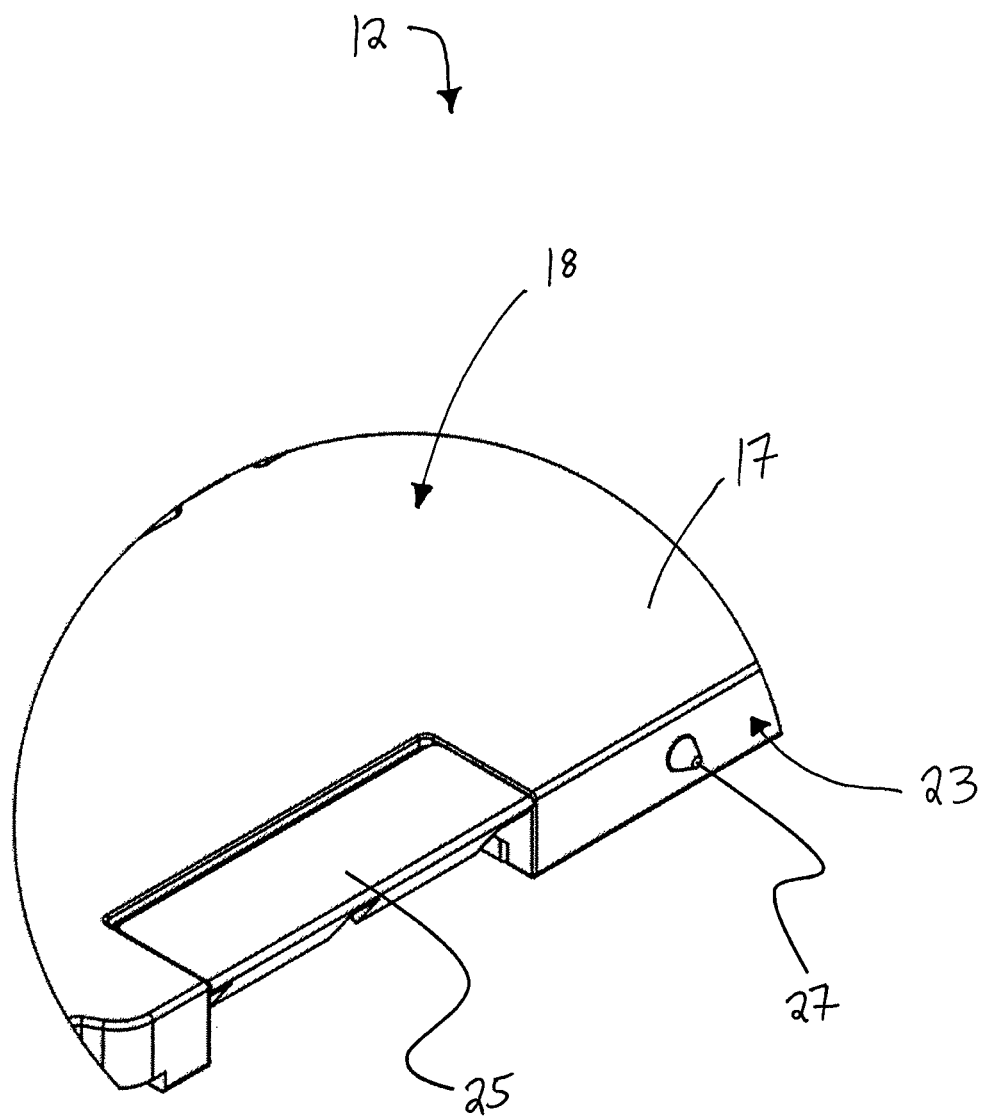
FIG. 6 is a partial top-side perspective view the trolley assembly of FIG. 5.
Figure 7:
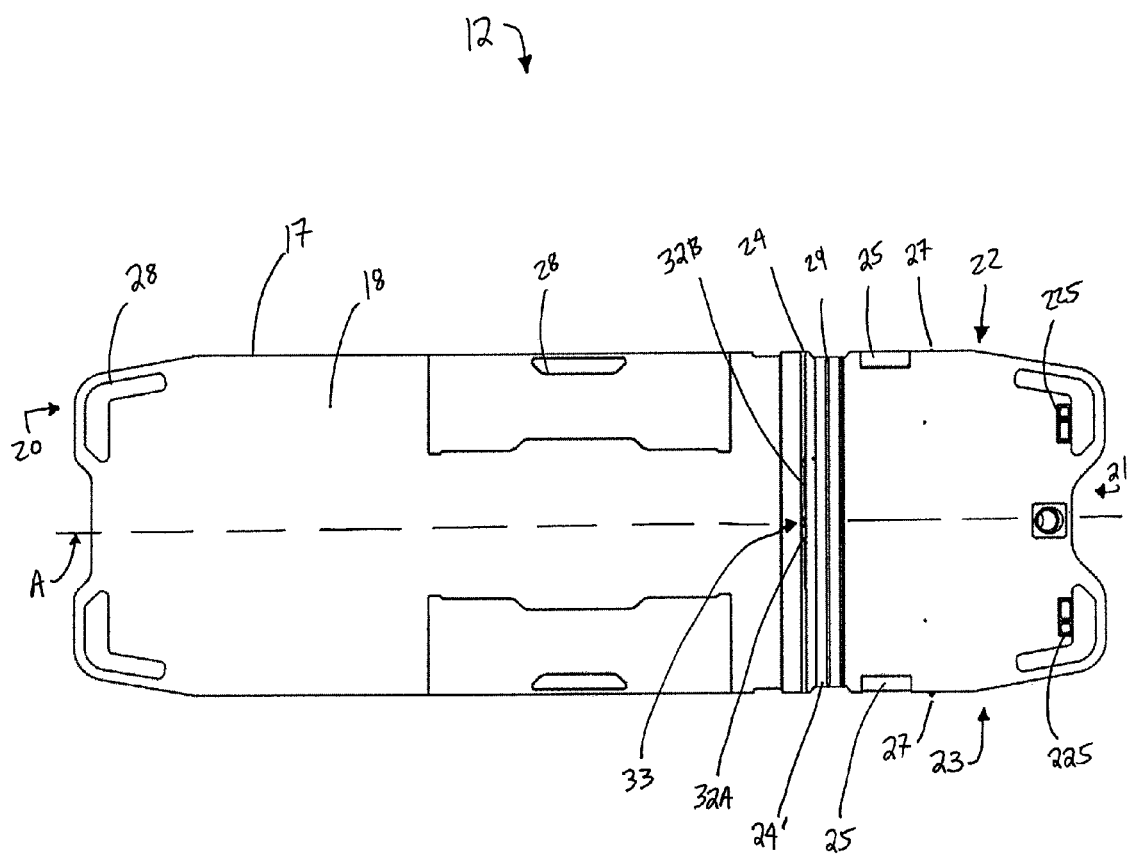
FIG. 7 is a top view of the trolley assembly of FIG. 5.

In exemplary embodiments, supporting frame 17 of trolley assembly 12 includes one or more fastener members 25 (e.g., docking hooks 25), and one or more interlock members 27 (interlock pin members 27). In certain embodiments and as shown in FIGS. 5-7, first side 22 includes one fastener member 25 and one interlock member 27, and second side 23 includes one fastener member 25 and one interlock member 27. As discussed further below, each fastener member 25 is configured to releasably fasten or attach to various target modality assemblies 16 (e.g., to a securement member 125 of assembly 16), and each exemplary interlock member 27 extends from its respective side 22, 23 and is configured to mate/interact with various target modality assemblies 16 for patient transporting purposes.

In certain embodiments, the top side 18 of the supporting frame 17 of trolley assembly 12 includes one or more grooves 24. In exemplary embodiments and as shown in FIGS. 5-12, top side 18 includes two grooves 24, 24'. However and as discussed below, it is noted that in some embodiments the top side 18 may not include one or more grooves 24 for patient transporting purposes. In other embodiments, top side 18 may only include groove 24 and not groove 24', and vice versa.

In exemplary embodiments, each groove 24, 24' extends across the top side 18 from the first side 22 to the second side 23. In general and as further discussed below, each groove 24, 24' is configured and dimensioned to releasably mate or mount with respect to transfer assembly 14 (e.g., the bottom side 40 of transfer assembly 14) for patient transporting purposes. In exemplary embodiments, top side 18 (e.g., each groove 24, 24') is configured to releasably mate or un-mate with transfer assembly 14 from either side 22, 23 of supporting frame 17 (e.g., transfer assembly 14 can be loaded or unloaded from either side 22, 23 of trolley assembly 12).

Figure 16:
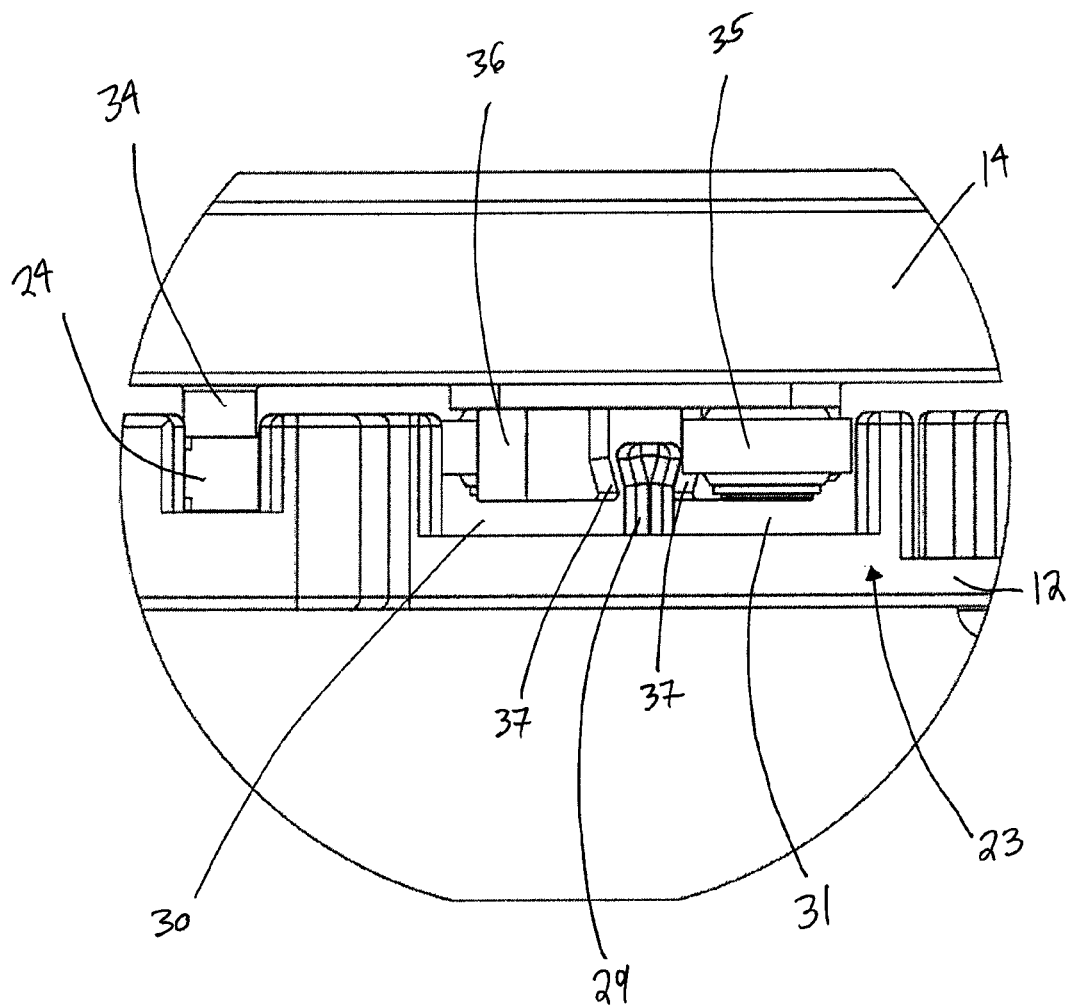
FIG. 16 is a partial side view of the trolley assembly and transfer assembly of FIG. 11, with the transfer assembly releasably mounted with respect to the trolley assembly.

In certain embodiments and as shown in FIGS. 5, 7, 8 and 16, groove 24' includes a wall member 29 that extends from the first side 22 to the second side 23. Exemplary wall member 29 is positioned substantially in the middle of groove 24' and defines first groove section 30 and second groove section 31 of groove 24' (FIG. 8), although the present disclosure is not limited thereto. Rather, wall member 29 may be positioned at any suitable location in groove 24' (and/or in groove 24). In other embodiments, groove 24' does not include wall member 29. As discussed further below, exemplary groove 24 (e.g., each groove section 30, 31) is configured and dimensioned to releasably engage or mate with extending members 35 and/or guide members 36 of transfer assembly 14 (FIG. 16). As noted below, at least a portion of the top side 37 (FIG. 16) of each guide member 36 (or extending member 35) can taper or extend outwardly to ensure that releasably mated transfer assembly 14 cannot be removed from supporting frame 17 of trolley assembly 12 (e.g., from groove 24' and/or wall member 29) by lifting on the transfer assembly 14 in an upwards vertical direction (e.g., transfer assembly 14 can be released from engagement with supporting frame 17 by moving the transfer assembly 14 laterally towards side 22 or 23).

Figure 8:
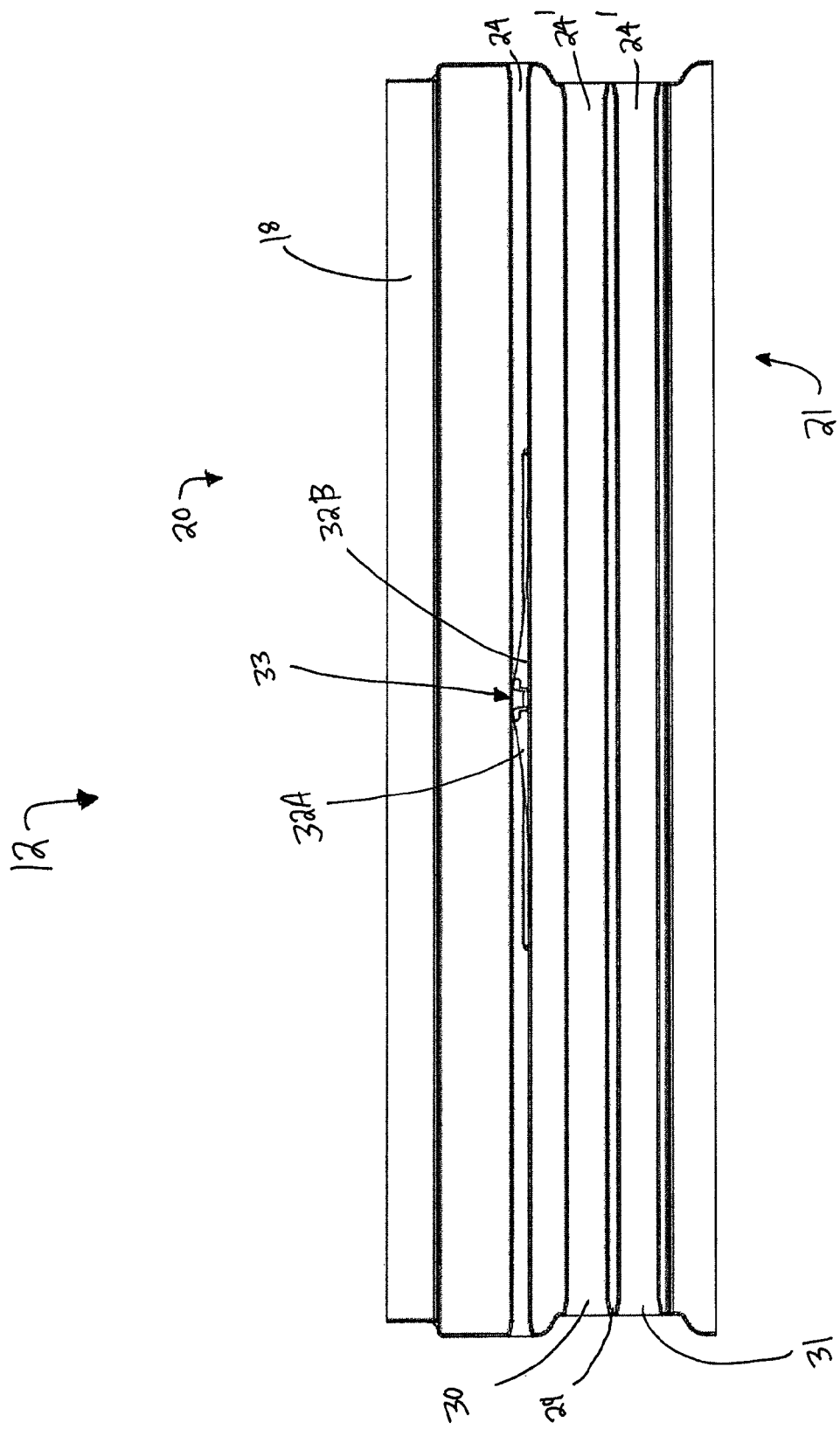
FIG. 8 is a partial top view of the trolley assembly of FIG. 7.
Figure 9:
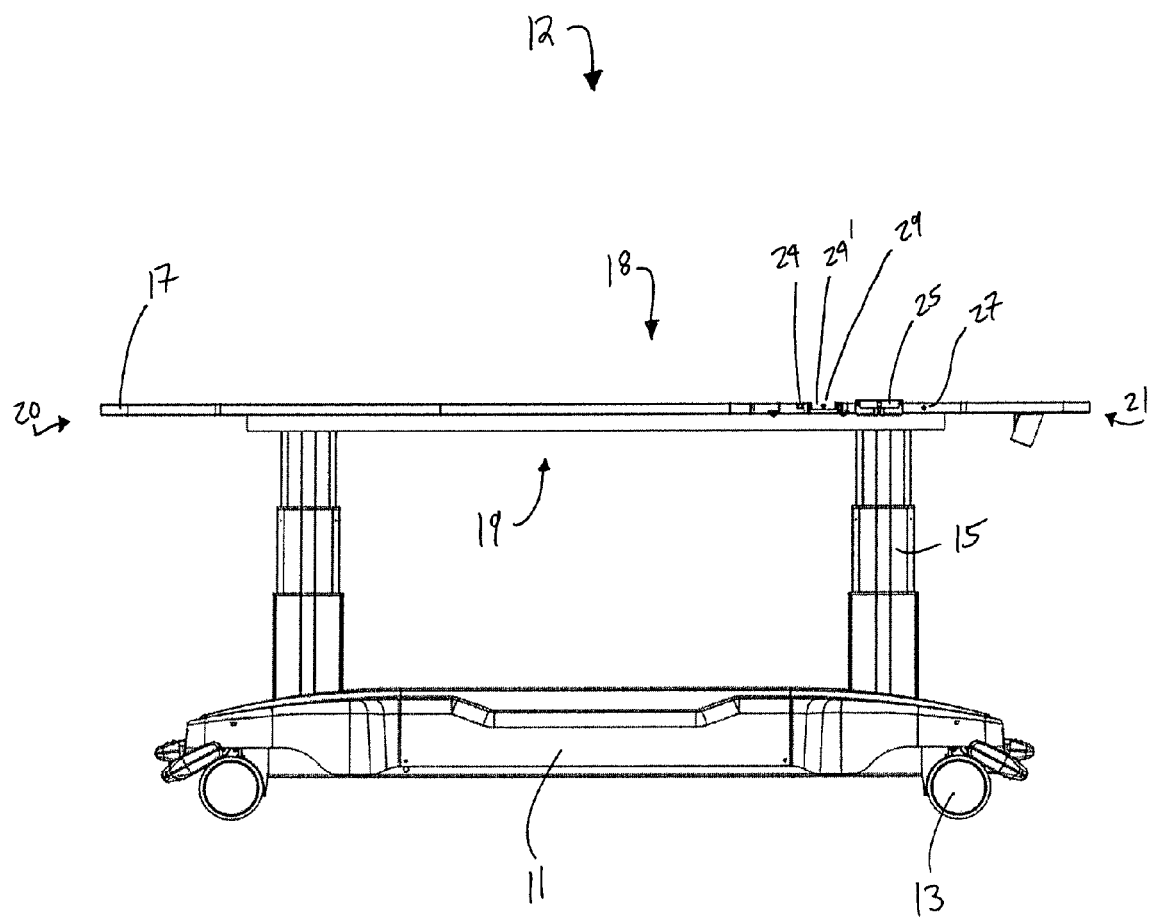
FIG. 9 is a side view of the trolley assembly of FIG. 5.

In exemplary embodiments, groove 24 (or groove 24') of supporting frame 17 includes or is associated with one or more safety latching members 32. As shown in FIG. 8, groove 24 can include or be associated with two latching members 32A, 32B. In certain embodiments and as discussed further below, the two latching members 32A, 32B are positioned adjacent to one another at least partially within groove 24 and define a safety member recess or catch 33, when the latching members 32A, 32B are in the safety position. In exemplary embodiments, safety member recess 33 is positioned substantially along the central longitudinal axis A of supporting frame 17 (FIG. 7), although the present disclosure is not limited thereto. Rather, safety member recess 33 (if present) may be positioned at any suitable location relative to supporting frame 17.

Figure 14:
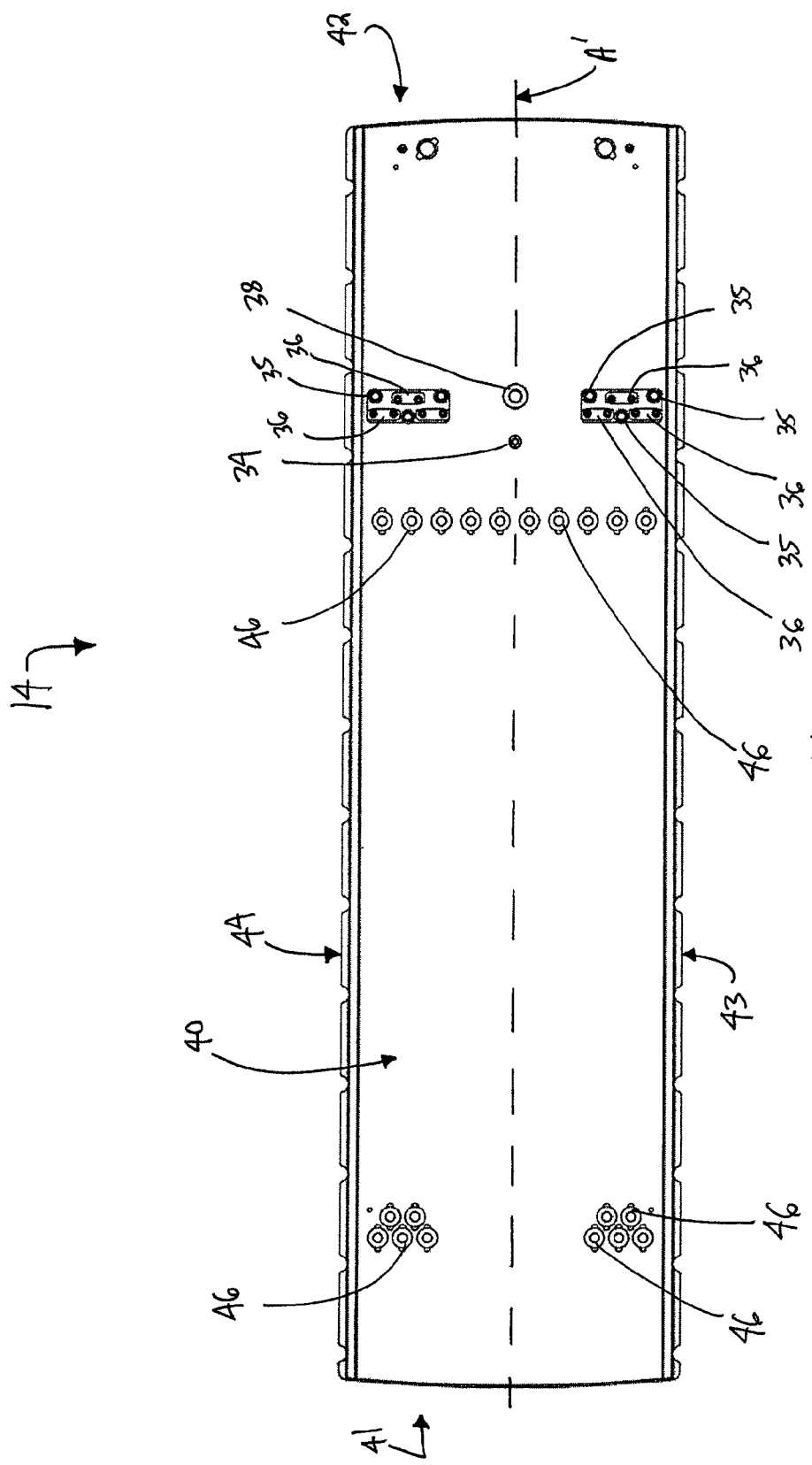
FIG. 14 is a bottom view of the transfer assembly of FIG. 13.
Figure 15:
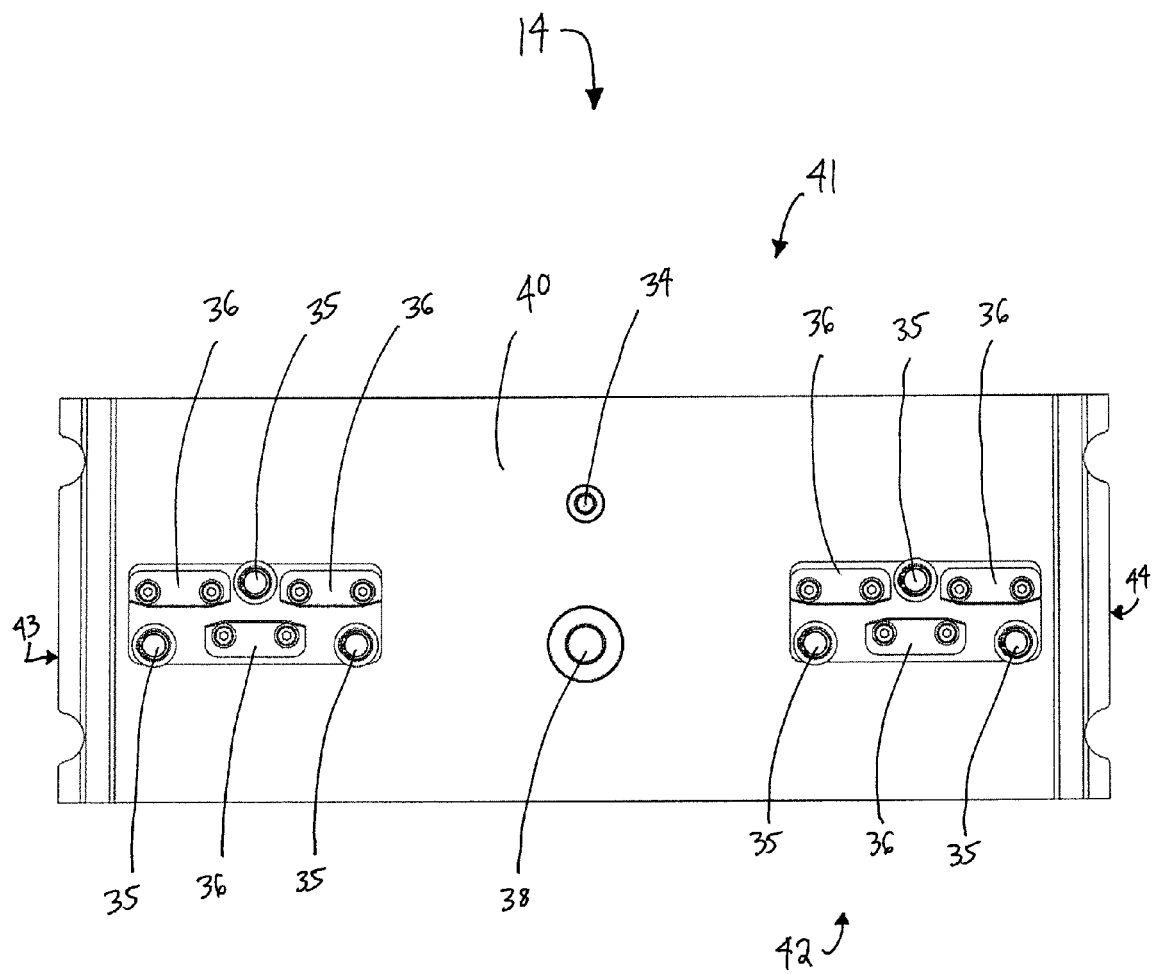
FIG. 15 is a partial bottom view of the transfer assembly of FIG. 14.

As discussed further below, exemplary groove 24 and/or safety member recess 33 is configured and dimensioned to releasably engage or mate with safety member 34 (e.g., safety pin member 34) of transfer assembly 14 (FIGS. 15-16). Transfer assembly 14 can also include locating member 38 (e.g., locating pin member 38), as discussed further below in connection with transfer assembly 14. In exemplary embodiments, safety member 34 and/or locating member 38 are positioned substantially along the central longitudinal axis A' of the bottom side 40 of transfer assembly 14 (FIG. 14), although the present disclosure is not limited thereto. Rather, safety member 34 and/or locating member 38 (if present) may be positioned at any suitable location relative to transfer assembly 14.

As shown in FIGS. 1-3 and 11-16, transfer assembly 14 (or 14') of patient transport system 10 is configured and dimensioned to have a patient 2 positioned and/or immobilized thereon for patient transporting and/or treatment purposes. In general, transfer assembly 14 is configured to be moved (e.g., slid) from trolley assembly 12 to a target modality assembly 16 (e.g., imaging or treatment modality 16) and/or from a target modality assembly 16 to trolley assembly 12 (e.g., assembly 14 can advantageously be moved by one person alone). While the transfer assembly 14 (and patient 2) are on the trolley assembly 12, the patient 2/assembly 14 can be transported to and from the various/different treatment/imaging locations 16.

Figure 11:
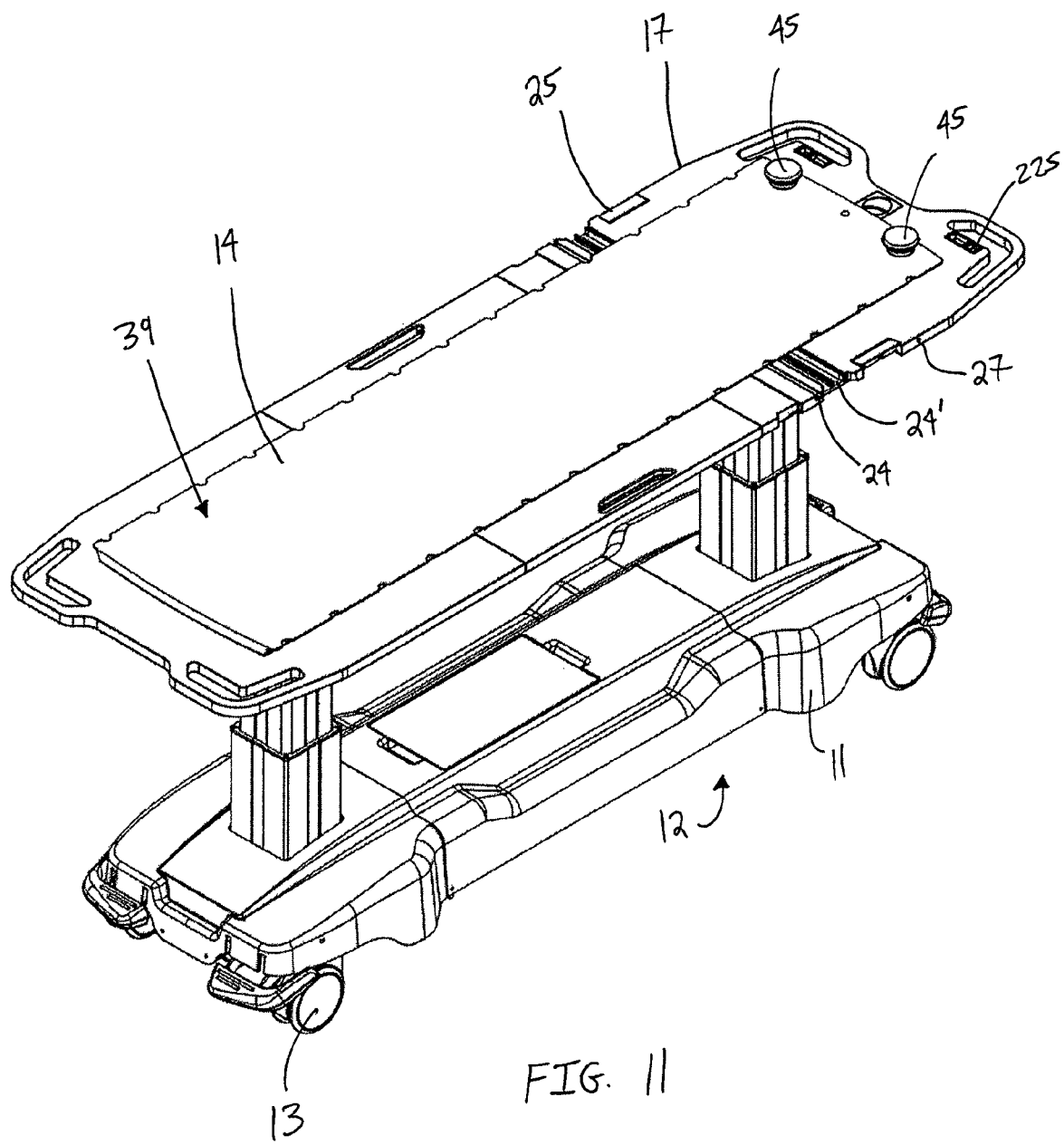
FIG. 11 is a top-side perspective view of the trolley assembly of FIG. 5, after an exemplary transfer assembly is releasably mounted thereon.
Figure 12:
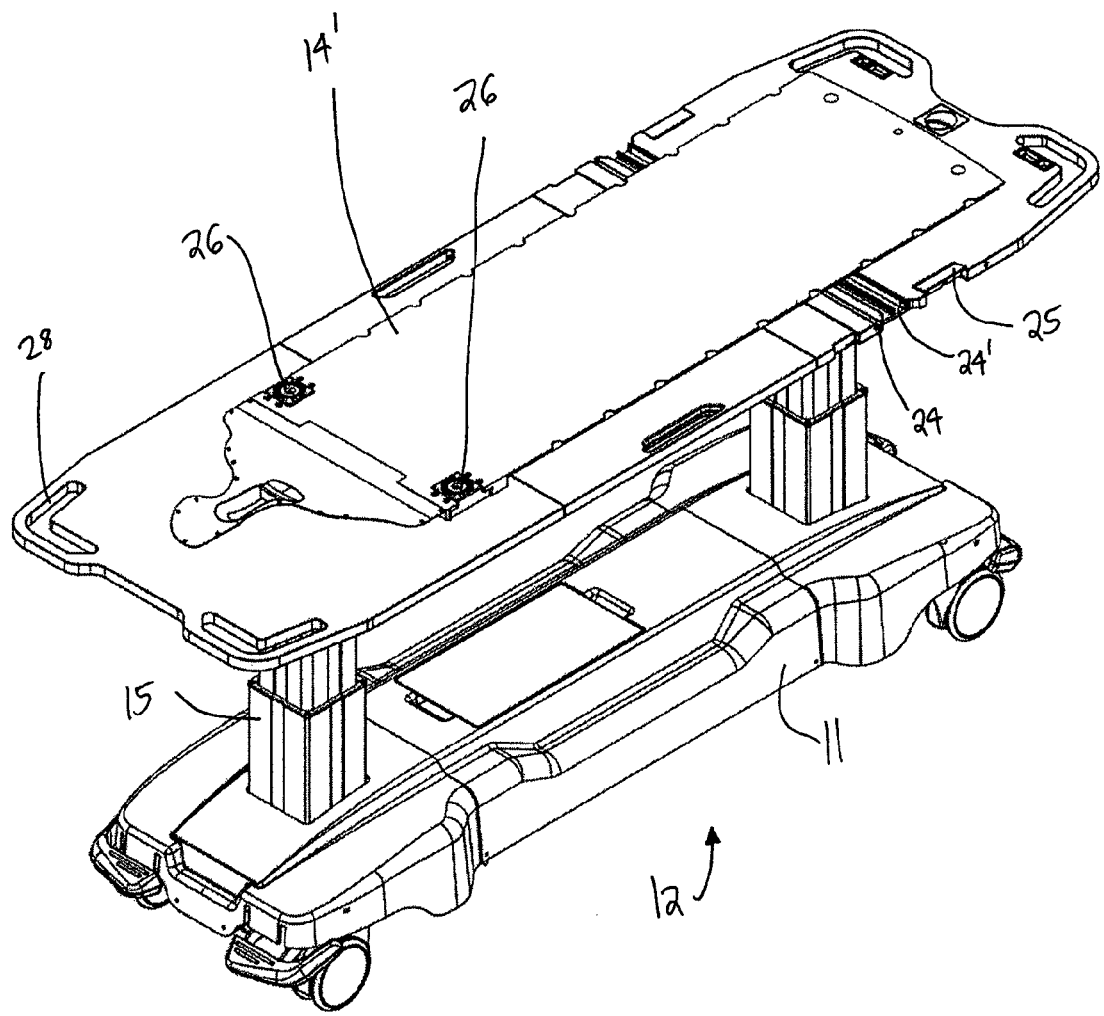
FIG. 12 is a top-side perspective view of the trolley assembly of FIG. 5, after another exemplary transfer assembly is releasably mounted thereon.
Figure 13:
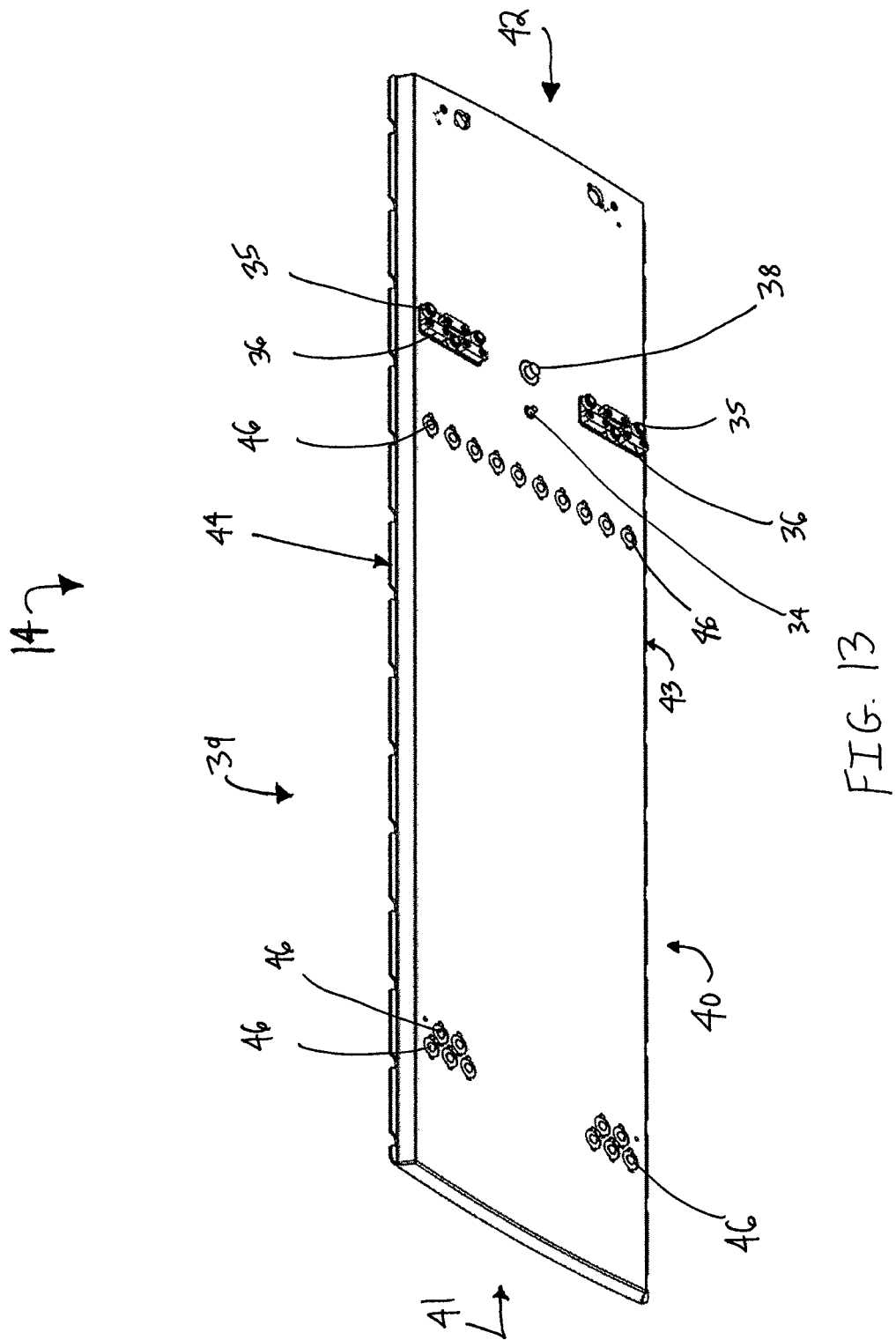
FIG. 13 is a bottom-side perspective view of an exemplary transfer assembly according to the present disclosure.

It is noted that transfer assembly 14 can be fabricated from a variety of materials and/or combination of materials (e.g. carbon fiber, Aramid (Kevlar), fiberglass, etc.), and can take a variety of shapes, styles and/or designs (e.g., transfer assembly 14 as shown in FIG. 11, or transfer assembly 14' as shown in FIG. 12, etc.). For example, transfer assembly 14' (or 14) can include various attaching and/or positioning features, accessories and/or structures 26 utilized to position/immobilize the patient 2 (e.g., leg stirrups, cushions, other immobilization devices, etc.).

As noted, transfer assembly 14 (or 14') is configured and dimensioned to be utilized in conjunction with a wide variety of imaging and/or treatment modalities, environments or assemblies 16. For example, the target modality assemblies 16 that the patient 2 may be transported to and/or from (e.g., via the trolley assembly 12 and transfer assembly 14) may include many different types of equipment/surfaces (e.g., radiation therapy treatment tables/surfaces, CT tables/surfaces, MRI tables/surfaces, brachytherapy tables/surfaces, etc.). In general, patient transport system 10 allows a patient 2 to be positioned or immobilized on a transfer assembly 14 (e.g., on transfer assembly 14 which is positioned on trolley assembly 12), and then transferred (e.g., laterally transferred from the trolley assembly 12) onto the surface of a target modality assembly 16 (e.g., target modality) for various purposes/applications/treatments. Exemplary transfer assembly 14, 14' is compatible with a variety of diagnostic imaging, radiation therapy applications and/or treatment modalities or the like.

In general, transfer assembly 14 includes a top side 39, bottom side 40, first end 41, second end 42, first side 43 and second side 44. In certain embodiments, top side 39 of transfer assembly 14 defines a substantially planar top side or surface 39 that is configured to allow a patient 2 to be positioned or immobilized thereon. Exemplary transfer assembly 14 includes one or more user-friendly handles 45 for patient transporting purposes.

It is noted that in addition to or in lieu of safety member 34, extending members 35, guide members 36, and/or locating member 38, the transfer assembly 14 (e.g., bottom side 40 of transfer assembly 14) and/or system 10 can include rollers 46 (e.g., plastic rollers), roller bearings, air bearings, air bladders, slides, air platforms, opposing low friction materials/interfaces and/or other low friction devices/surfaces, etc., for the low-friction transfer/movement of transfer assembly 14 (e.g., for the movement of transfer assembly 14 from the trolley assembly 12 to the target modality assembly 16, and vice versa), as described and disclosed in U.S. Patent Pub. No. 2013/0212806, and U.S. Patent Application Ser. Nos. 61/865, 539, the entire contents of each being hereby incorporated by reference in their entireties.

In exemplary embodiments, the safety member 34, extending members 35, guide members 36, and/or locating member 38 extend from the bottom side 40 of the transfer assembly 14, and are configured and dimensioned to releasably engage or mate with the trolley assembly 12 (e.g., mate with grooves 24, 24' and their associated components/members, as discussed above/below) and/or with the target modality assembly 16 (e.g., mate with grooves 124, 124' and their associated components/members, as discussed above/below). In other embodiments, it is noted that transfer assembly 14 (e.g., bottom side 40) can include grooves and associated components/members similar to grooves 24 and/or 24' (or 124, 124'), and trolley assembly 12 (e.g., top side 18) and/or target modality assembly 16 (e.g., top side 118) can include safety members, extending members, guide members, and/or locating members (e.g., similar to safety member 34, extending members 35, guide members 36, and/or locating member 38) that are configured and dimensioned to releasably engage or mate with transfer assembly 14 for patient transporting purposes.

In certain embodiments, bottom side 40 includes one or more extending members 35 and one or more guide members 36. Exemplary extending members 35 take the form of bearings or balls or the like, although the present disclosure is not limited thereto. Rather, extending members 35 (and guide members 36) can take a variety of shapes/forms.

Figure 22:
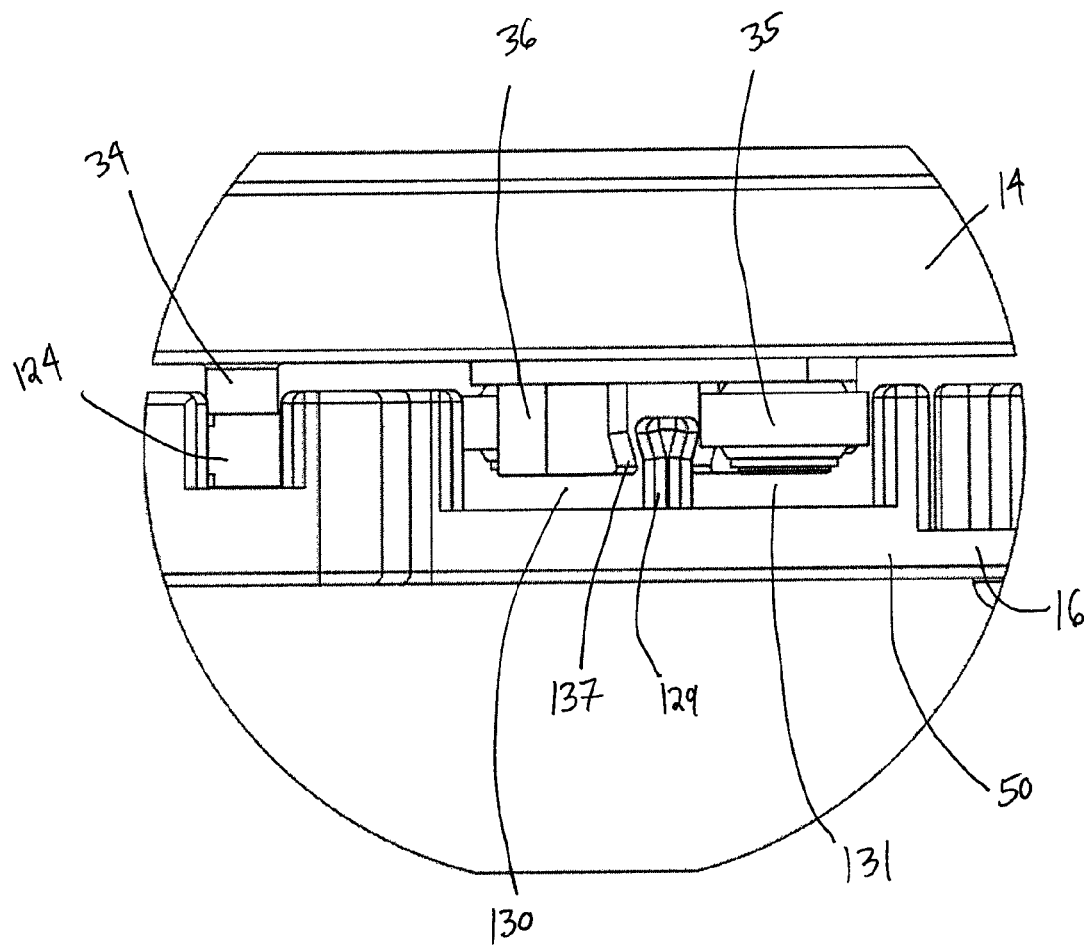
FIG. 22 is a partial side view of the target modality assembly and transfer assembly, with the transfer assembly releasably mounted with respect to the target modality assembly.

In general, exemplary grooves 24, 24' 124 and/or 124' are configured and dimensioned to releasably engage or mate with extending members 35 and/or guide members 36 of transfer assembly 14 (FIGS. 16 and 22). As noted and in some embodiments, at least a portion of the top side 37 (FIGS. 16 and 22) of each guide member 36 (or extending member 35) can taper or extend outwardly to ensure that releasably mated transfer assembly 14 cannot be removed from grooves 24, 24' 124 and/or 124' by lifting on the transfer assembly 14 in an upwards vertical direction.

Exemplary safety member 34 and locating member 38 extend from the bottom side 40 of the transfer assembly 14, and are configured and dimensioned to releasably engage or mate with the trolley assembly 12 and/or target modality assembly 16. More particularly and in certain embodiments, safety member 34 is configured to be positioned in recess/catch 33 of trolley assembly 12 when the transfer assembly 14 is releasably mounted with respect to trolley assembly 12, and safety member 34 is configured to be positioned in recess/catch 133 of target modality assembly 16 when the transfer assembly 14 is releasably mounted with respect to target modality assembly 16.

In exemplary embodiments, when the safety member 34 is engaged with the safety member catch 133 of the target modality assembly 16, the transfer assembly 14 is prevented from moving laterally relative to the target modality assembly 16, thereby providing a highly advantageous safety feature (e.g., transfer assembly 14 will not slide off the opposite lateral side of target modality assembly 16 when loading assembly 14, etc.). Likewise, when the safety member 34 is engaged with the safety member catch 33 of the trolley assembly 12, the transfer assembly 14 is prevented from moving laterally relative to the trolley assembly 12, thereby providing a highly advantageous safety feature (e.g., transfer assembly 14 will not slide off the opposite lateral side of trolley assembly 12 when loading assembly 14, etc.).

Moreover, catches 33 and 133 provide that transfer assembly 14 can be accurately and repeatably loaded/positioned on assembly 12 and 16, respectively, at the same locations/positions (e.g., via the engagement of member 34 with catch 33, 133, and/or via the engagement of member 38 with member 54) after every transfer assembly 14 loading process. In exemplary embodiments, after transfer assembly 14 is releasably mounted with respect to target modality assembly 16 (e.g., safety member 34 is engaged with the safety member catch 133 of the target modality assembly 16), at least a portion of the transfer assembly 14 and/or target modality assembly 16 is configured and dimensioned to be moved (e.g., longitudinally moved) relative to treatment or imaging equipment or the like for patient treatment/imaging purposes or the like.

Similarly, locating member 38 is configured to be positioned relative to locking member 54 of target modality assembly 16 when the transfer assembly 14 is releasably mounted with respect to target modality assembly 16. In certain embodiments and as discussed further below, when the transfer assembly 14 is moved to the target modality assembly 16, the locating member 38 engages with the locking member 54 and allows a user to accurately and repeatably locate and rigidly lock (e.g., in one location) the transfer assembly 14 to the target modality assembly 16 in a releasable manner. In some embodiments, the locating member 38 and locking member 54 are configured to allow the user to accurately and repeatably locate and rigidly lock in one location the transfer assembly 14 to the target modality assembly 16 to the level of sub-millimeter accuracy (e.g., which can be important for precise tumor targeting, etc.).

In exemplary embodiments, when the transfer assembly 14 is releasably mounted to the target modality assembly 16, the safety member catch 133 and the safety member 34 are positioned outside of the treatment or imaging area of the target modality assembly 16. Similarly and in certain embodiments, when the transfer assembly 14 is releasably mounted to the target modality assembly 16, the locking member 54 and the locating member 38 are positioned outside of the treatment or imaging area of the target modality assembly 16.

It is noted that trolley assembly 12 may or may not include a locking member (e.g., similar to member 54) that interacts, mates and/or engages with locating member 38 when the transfer assembly 14 is releasably mounted with respect to trolley assembly 12.

With reference to FIGS. 1-4 and 17-22, there is illustrated an embodiment of an exemplary target modality assembly 16 according to the present disclosure. In general and as noted above, target modality assembly 16 (or 16'—FIGS. 27-28) is configured and dimensioned for patient transporting and/or imaging/treatment purposes. It is noted that target modality assembly 16, 16' can take a variety of forms and/or designs.

In exemplary embodiments, target modality assembly 16 includes a back panel member 50. Support beams 51 can be mounted with respect to and/or extend from back panel member 50, and assembly 16/member 50 can include indexing members 52 or the like, as described and disclosed in U.S. Patent Pub. No. 20007/0074347, the entire contents of which is hereby incorporated by reference in its entirety.

In general, back panel member 50 includes a top side 118, bottom side 119, first end 120, second end 121, first side 122 and second side 123. In certain embodiments and as discussed in further detail below, top side 118 of back panel member 50 defines a substantially planar top side or surface 118 and includes structures/features (e.g., grooves 124, 124') that are configured and dimensioned to releasably mount with respect to patient transfer assembly 14. Exemplary back panel member 50 of target modality assembly 16 includes one or more user-friendly locating/locking handle 53, as discussed further below.

In exemplary embodiments, back panel member 50 includes one or more securement members 125 (e.g., docking latches 125), and one or more interlock members 127 (interlock pin members 127). In certain embodiments, first side 122 includes one securement member 125 and one interlock member 127, and second side 123 includes one securement member 125 and one interlock member 127. As discussed further below, each securement member 125 is configured to releasably fasten, attach or secure to various trolley assemblies 12, and each exemplary interlock member 127 extends from its respective side 122, 123 and is configured to mate/interact with various trolley assemblies 12 for patient transporting purposes.

Figure 17:
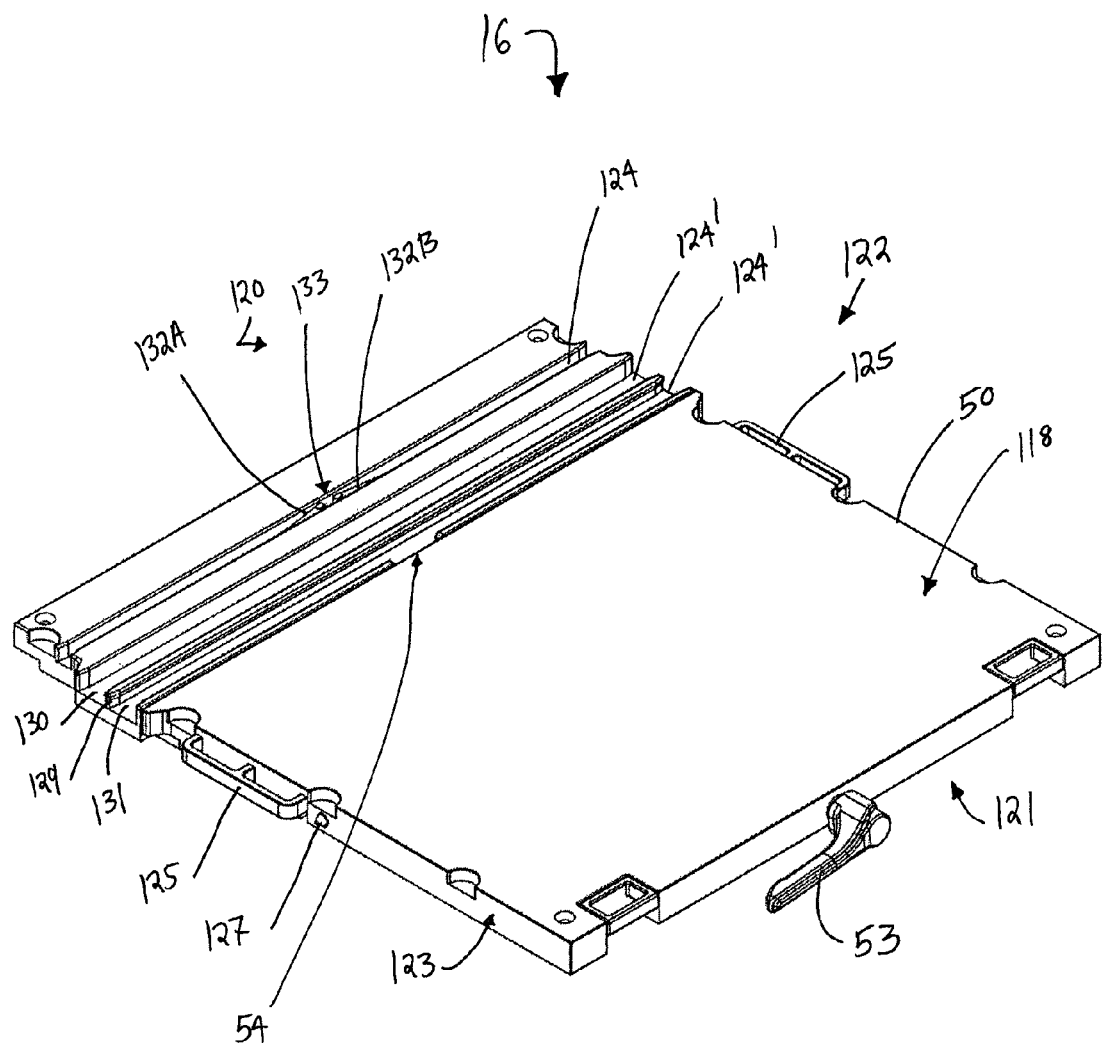
FIG. 17 is a partial top-side perspective view of an exemplary target modality assembly according to the present disclosure.
Figure 18A:
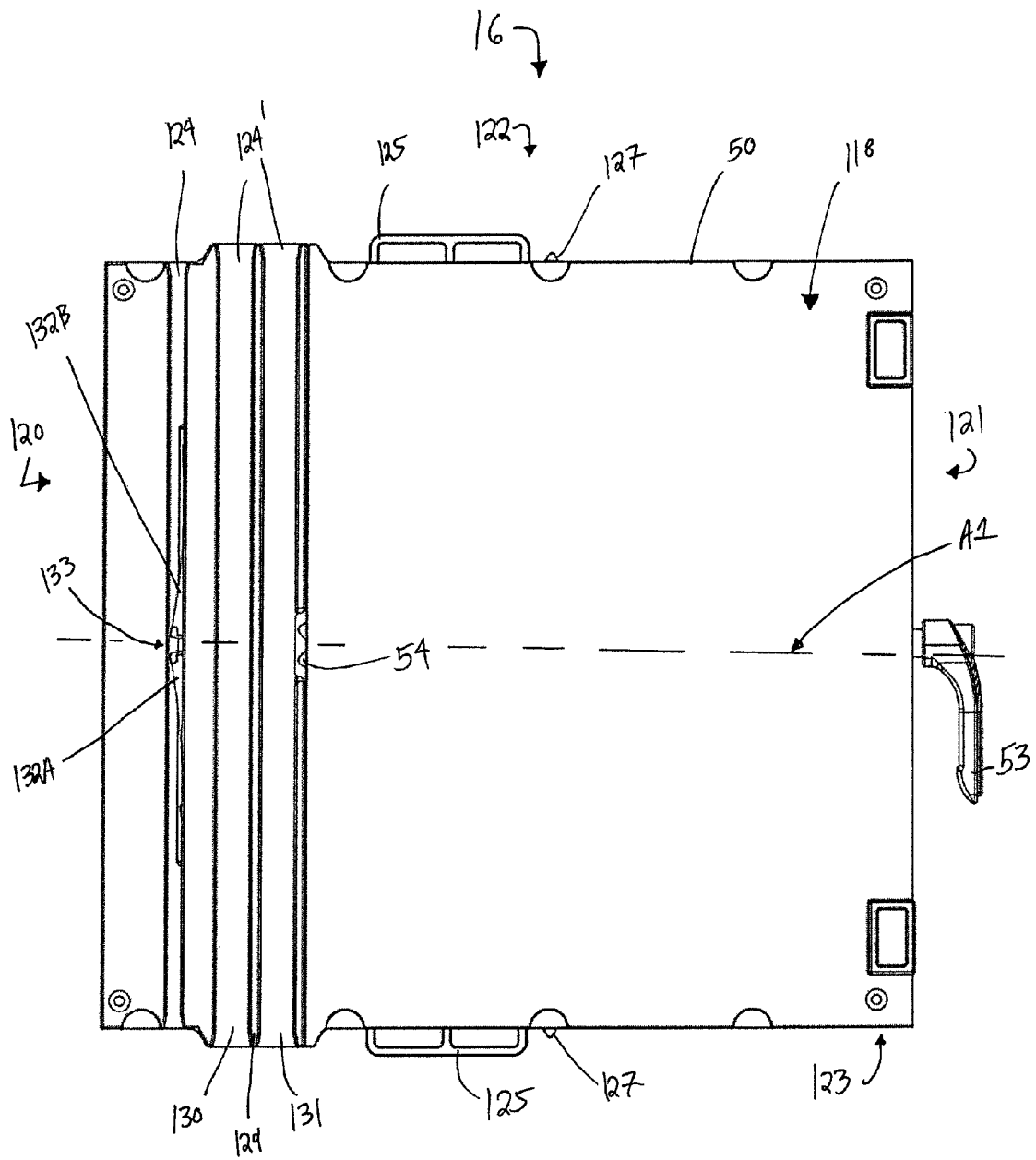
FIG. 18A is a top view of the target modality assembly of FIG. 17.

In certain embodiments, the top side 118 of the back panel member 50 includes one or more grooves 124. In exemplary embodiments and as shown in FIGS. 17-19, top side 118 includes two grooves 124, 124'. However, it is noted that in some embodiments the top side 118 may not include one or more grooves 124 for patient transporting purposes. In other embodiments, top side 118 may only include groove 124 and not groove 124', and vice versa.

In exemplary embodiments, each groove 124, 124' extends across the top side 118 from the first side 122 to the second side 123. In general and as further discussed below, each groove 124, 124' is configured and dimensioned to releasably mate or mount with respect to transfer assembly 14 (e.g., the bottom side of transfer assembly 14) for patient transporting purposes. In exemplary embodiments, top side 118 (e.g., each groove 124, 124') is configured to releasably mate or un-mate with transfer assembly 14 from either side 122, 123 of back panel member 50 (e.g., transfer assembly 14 can be loaded or unloaded from either side 122, 123 of target modality assembly 16).

In certain embodiments and as shown in FIGS. 17-19 and 22, groove 124' includes a wall member 129 that extends from the first side 122 to the second side 123. Exemplary wall member 129 is positioned substantially in the middle of groove 124' and defines first groove section 130 and second groove section 131 of groove 124' (FIG. 18A), although the present disclosure is not limited thereto. Rather, wall member 129 may be positioned at any suitable location in groove 124' (and/or in groove 124). In other embodiments, groove 124' does not include wall member 129. As discussed further below, exemplary groove 124 (e.g., each groove section 130, 131) is configured and dimensioned to releasably engage or mate with extending members 35 and/or guide members 36 of transfer assembly 14 (FIG. 22). As noted below, at least a portion of the top side 37 (FIG. 22) of each guide member 36 (or extending member 35) can taper or extend outwardly to ensure that releasably mated transfer assembly 14 cannot be removed from back panel member 50 of target modality assembly 16 (e.g., from groove 124' and/or wall member 129) by lifting on the transfer assembly 14 in an upwards vertical direction (e.g., transfer assembly 14 can be released from engagement with back panel member 50 by moving the transfer assembly 14 laterally towards side 122 or 123).

In exemplary embodiments, groove 124 (or groove 124') of back panel member 50 includes or is associated with one or more safety latching members 132. As shown in FIG. 18A, groove 124 can include or be associated with two latching members 132A, 132B. In certain embodiments and as discussed further below, the two latching members 132A, 132B are positioned adjacent to one another at least partially within groove 124 and define a safety member recess or catch 133, when the latching members 132A, 132B are in the safety position. In exemplary embodiments, safety member recess 133 is positioned substantially along the central longitudinal axis A1 of back panel member 50 (FIG. 18A), although the present disclosure is not limited thereto. Rather, safety member recess 133 (if present) may be positioned at any suitable location relative to back panel member 50.

As discussed further below, exemplary groove 124 and/or safety member recess 133 is configured and dimensioned to releasably engage or mate with safety member 34 (e.g., safety pin member 34) of transfer assembly 14 (FIGS. 15 and 22). As noted, transfer assembly 14 can also include locating member 38 (e.g., locating pin member 38—FIG. 15).

Figure 18B:
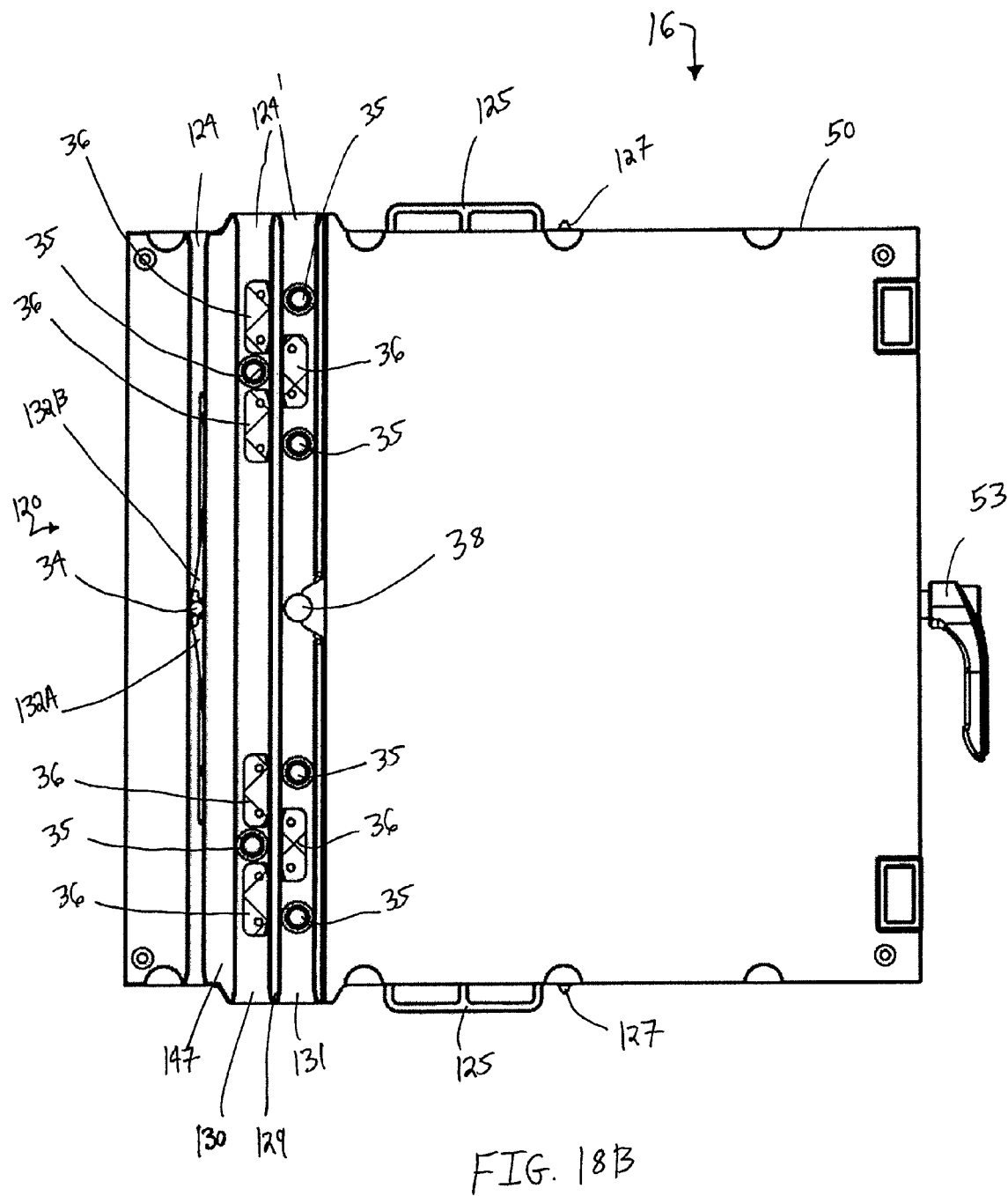
FIG. 18B is another top view of the target modality assembly of FIG. 17, showing features/structures of the transfer assembly positioned within the grooves of the target modality assembly.
Figure 18C:
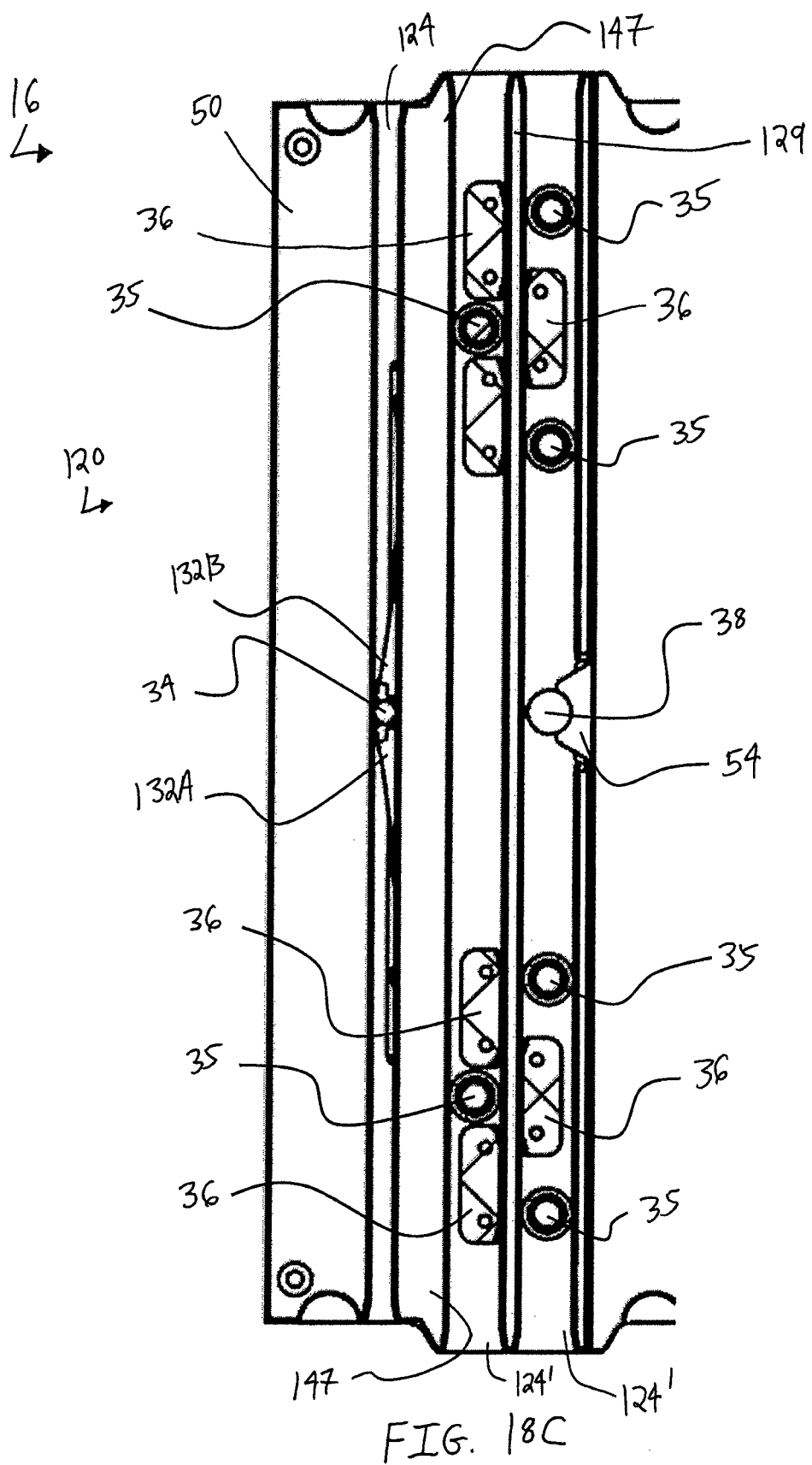
FIG. 18C is a partial exploded top view of the target modality assembly of FIG. 18B.
Figure 19:
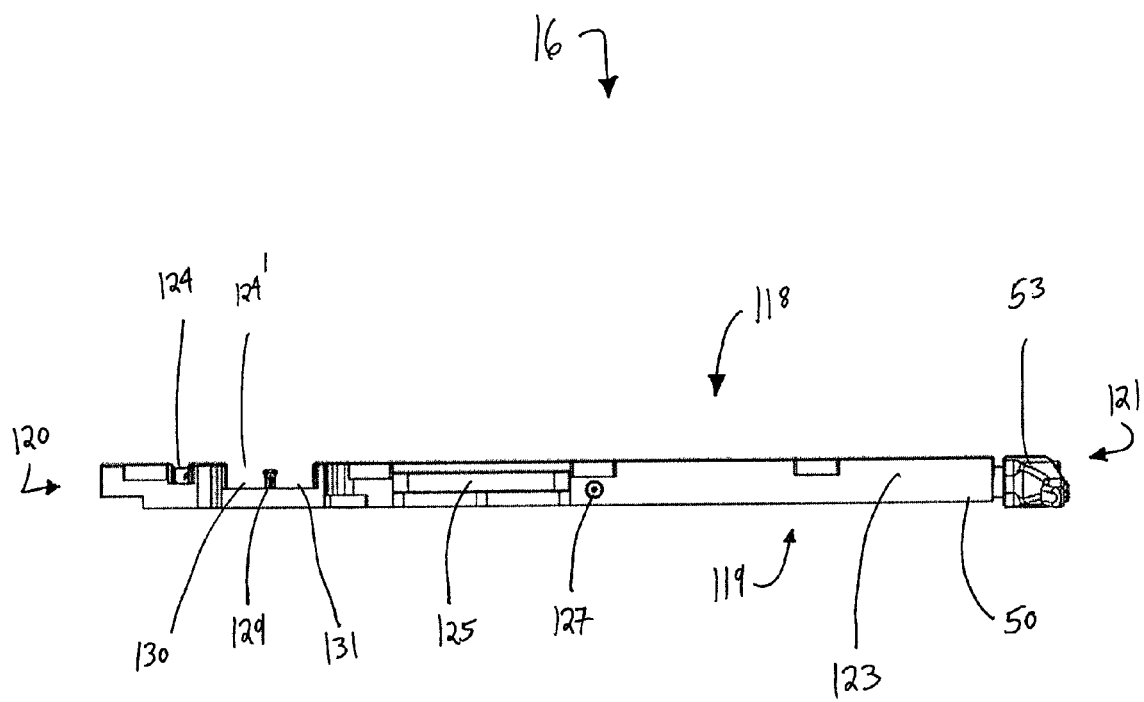
FIG. 19 is a side view of the target modality assembly of FIG. 17.

In exemplary embodiments and as shown in FIGS. 18A-C, groove 124' (e.g., second groove section 131) (or groove 124) of back panel member 50 includes or is associated with one or more locking/locating member 54. In exemplary embodiments, locking member 54 is positioned substantially along the central longitudinal axis A1 of back panel member 50 (FIG. 18A), although the present disclosure is not limited thereto. Rather, locking member 54 (if present) may be positioned at any suitable location relative to back panel member 50. As discussed further below, exemplary groove 124' and/or locking/locating member 54 is configured and dimensioned to releasably engage, lock or mate with locating member 38 (e.g., locating pin member 38) of transfer assembly 14 (FIGS. 15, 18B and 18C).

Figure 3:
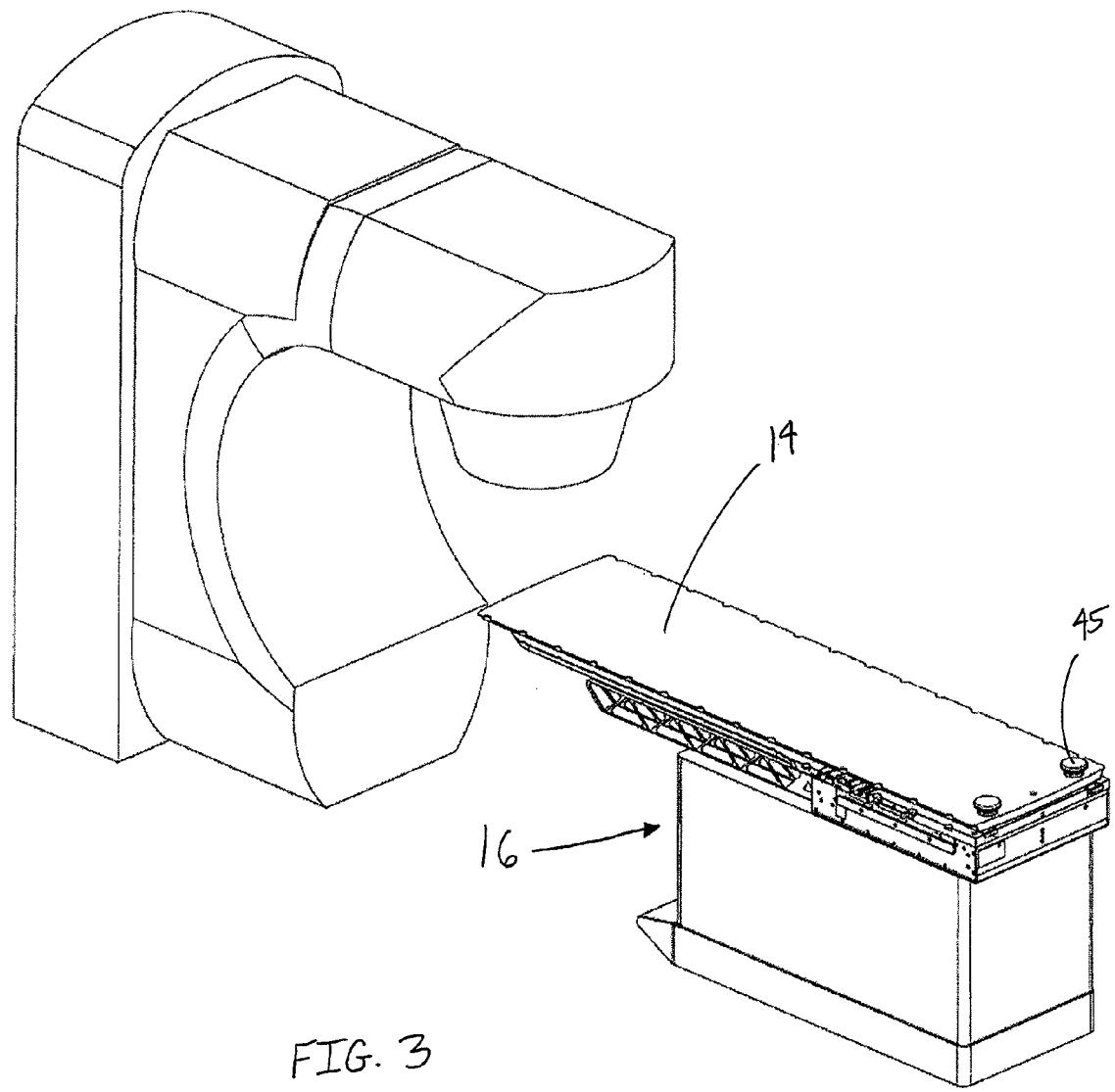
FIG. 3 is a side perspective view of an exemplary transfer assembly and target modality assembly.
Figure 4:
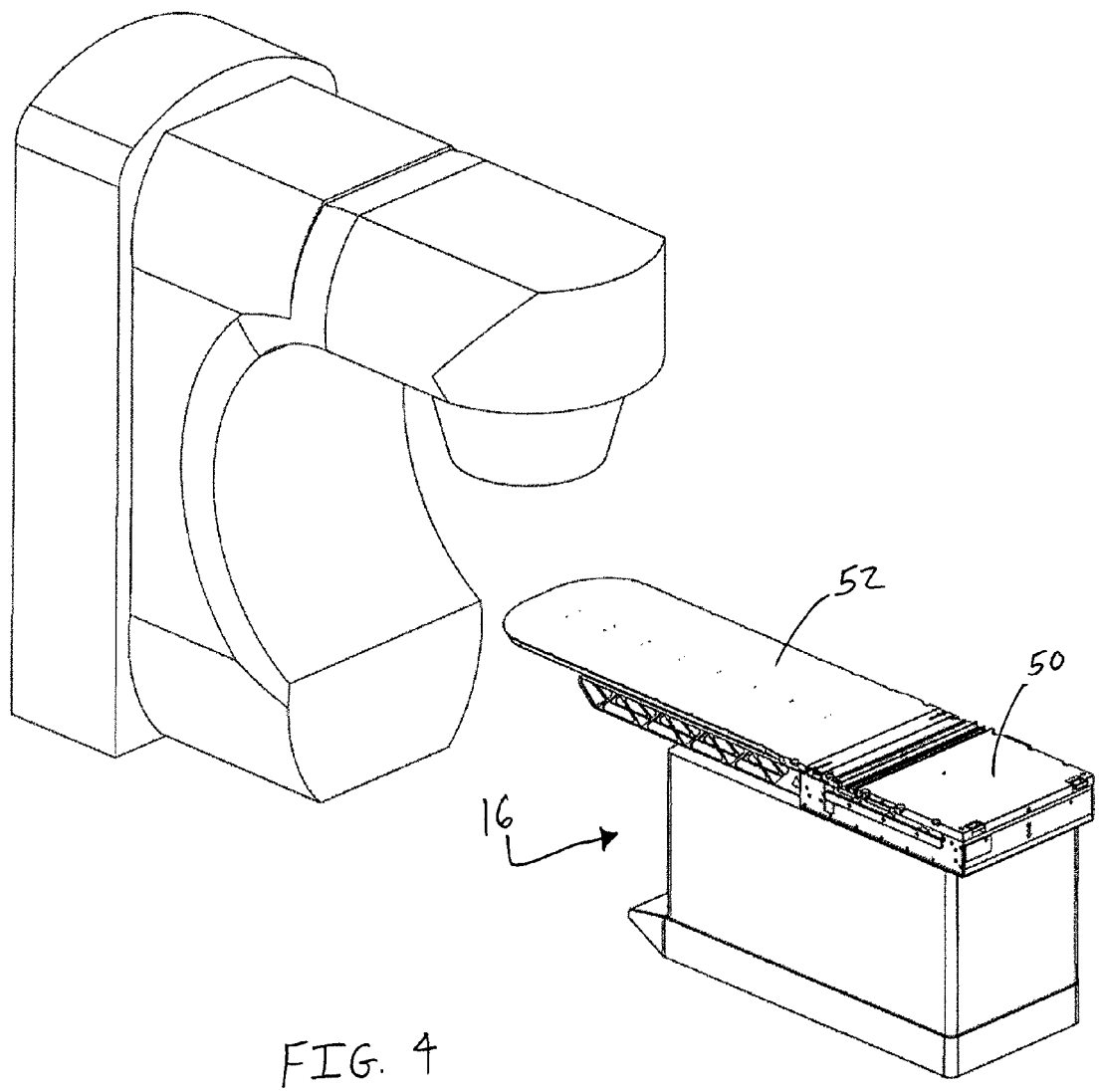
FIG. 4 is a side perspective view of an exemplary target modality assembly.

FIG. 3 depicts a transfer assembly 14 that is releasably mounted with respect to a target modality assembly 16. More particularly, the bottom side 40 of transfer assembly 14 includes a plurality of extending members 35 and guide members 36 that are releasably mated with the grooves 124, 124' of the top side 118 of the back panel 50 of the target modality assembly 16.

FIG. 2 depicts trolley assembly 12 positioned adjacent to target modality assembly 16. As such, a user can move the transfer assembly 14 that is releasably mounted with respect to target modality assembly 16 to the trolley assembly 12 (e.g., for patient transporting purposes via trolley assembly 12). As noted, the mounted transfer assembly 14 can be loaded or unloaded from either side 122, 123 of the back panel 50 of target modality assembly 16.

When the transfer assembly 14 is releasably mounted with respect to target modality assembly 16 as shown in FIG. 3, the safety member 34 is positioned in recess/catch 133 of target modality assembly 16 (FIGS. 18B-18C), and locating member 38 is positioned adjacent to and/or in engagement with locking member 54 (FIGS. 18B-18C). Moreover and as shown in FIGS. 18A-18C, each extending member 35 and guide member 36 of transfer assembly 14 is at least partially positioned within and/or engaged with groove 124' (or groove 124) of back panel 50.

To transfer/move the releasably mounted transfer assembly 14 from the target modality assembly 16 to trolley assembly 12, first a user can first position trolley assembly 12 adjacent to target modality assembly 16 as shown in FIG. 2. Again, however, it is noted that mounted transfer assembly 14 can be loaded or unloaded from either side 122, 123 of the back panel 50 of target modality assembly 16.

In exemplary embodiments, prior to or during placing trolley assembly 12 adjacent to target modality assembly 16, a user can pull the appropriate fastener member trigger 225 on trolley assembly 12 to raise/lift the fastener member 25 (e.g., docking hook) upwards. In certain embodiments, each side 22, 23 at second end 21 of trolley assembly 12 includes a fastener member trigger 225 that is configured to activate/lift its respective fastener member 25 on side 22 or 23. However, it is noted that triggers 225 can be located/positioned at any suitable location on assembly 12.

Once trolley assembly 12 is adjacent to target modality assembly 16 and positioned so that grooves 24, 24' substantially align with grooves 124, 124', the fastener member 25 releasably and securely engages/mates with securement member 125 (e.g., docking latch) of back panel 50. In certain embodiments, trolley assembly and target modality assembly 16 can include positioning markers or alignment markers or the like to facilitate the proper alignment of trolley assembly 12 with target modality assembly 16. Moreover and when assembly 12 is adjacent to target modality assembly 16, the respective interlock member 27 (e.g., interlock pin) of assembly 12 adjacent to target modality assembly 16 is engaged/mated with and/or depressed by assembly 16, and the respective interlock member 127 (interlock pin) of assembly 16 adjacent to assembly 12 is engaged/mated with and/or depressed by assembly 12. In certain embodiments, when assembly 12 is adjacent to target modality assembly 16, the respective interlock member 27 of assembly 12 adjacent to target modality assembly 16 is engaged/mated with and/or depressed by interlock member 127 of assembly 16 (and interlock member 127 of assembly 16 adjacent to assembly 12 is engaged/mated with and/or depressed by interlock member 27 of assembly 12).

In exemplary embodiments and as shown in FIG. 2, after the trolley assembly 12 is adjacent to target modality assembly 16 (positioned so that grooves 24, 24' substantially align with grooves 124, 124'), and fastener member 25 is releasably and securely engaged/mated with securement member 125, and the interlock member 27 adjacent to target modality assembly 16 is engaged/mated with and/or depressed by assembly 16, and the interlock member 127 adjacent to assembly 12 is engaged/mated with and/or depressed by assembly 12, the user is now ready to proceed further with the process of moving assembly 14 from assembly 16 to trolley 12.

Figure 20A:
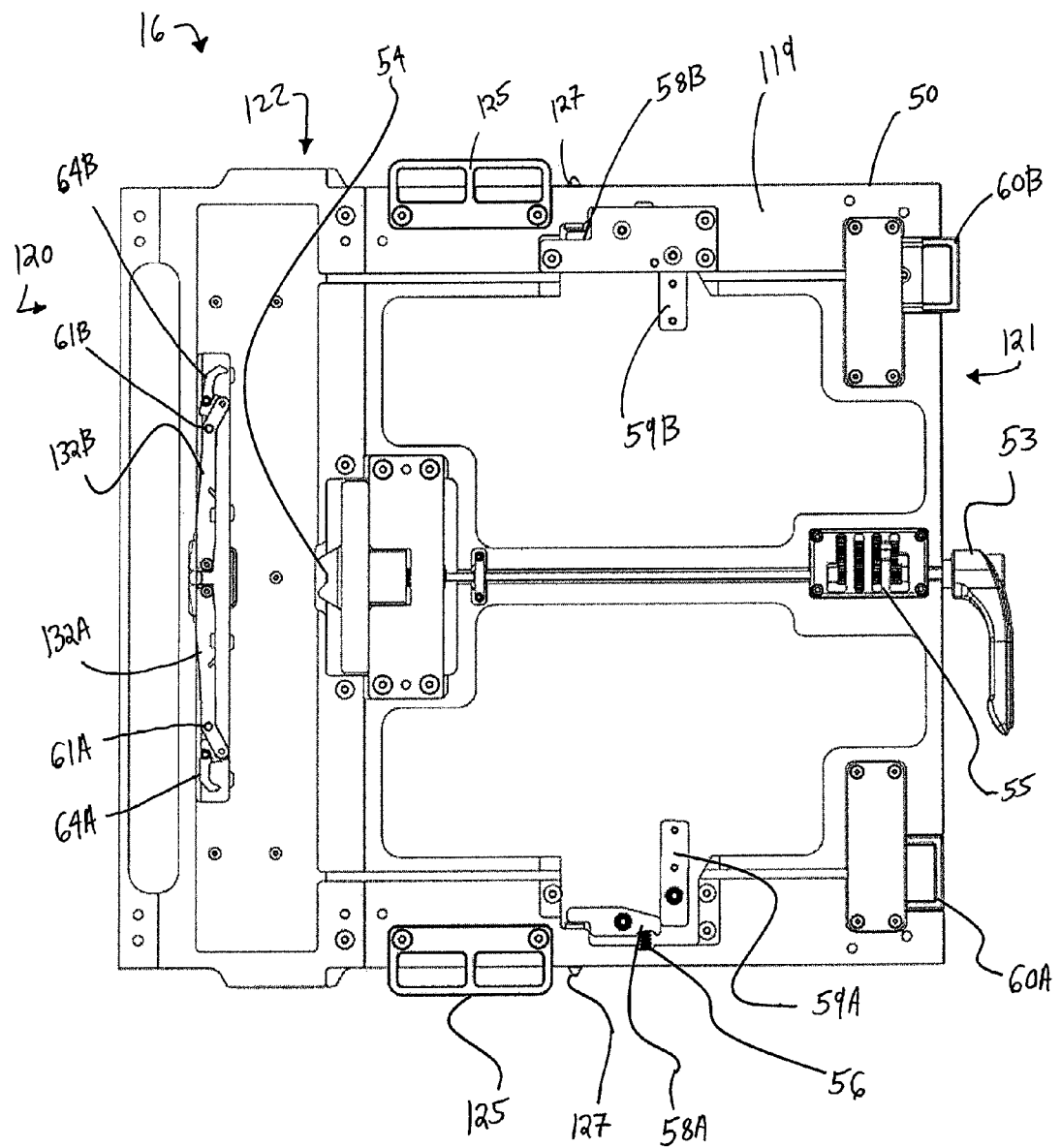
FIGS. 20A-20B are bottom views of the target modality assembly of FIG. 17.

However and as shown in FIG. 20A, prior to the interlock member 127 adjacent to assembly 12 being engaged/mated with and/or depressed by assembly 12, the interlock member 127 will not be depressed/engaged. Because of this and as shown in FIG. 20A, the interlock transfer member 58A associated with its respective interlock member 127 will be oriented/positioned (e.g., via spring member 56) to prevent its associated release cable pull member 59A from rotating (e.g., clockwise in FIG. 20A). Because the release cable pull member 59A cannot rotate in this position/orientation, the associated safety latch release pull trigger 60A cannot be pulled/activated/engaged, and its associated safety latch 132A will stay in place (e.g., will keep safety pin 34 in recess 133). The same safety functionality applies to interlock member 127 on side 122, and to its associated interlock transfer member 58B, release cable pull member 59B, safety latch release pull trigger 60B and safety latch 132B, as shown in FIG. 20A.

Figure 20B:
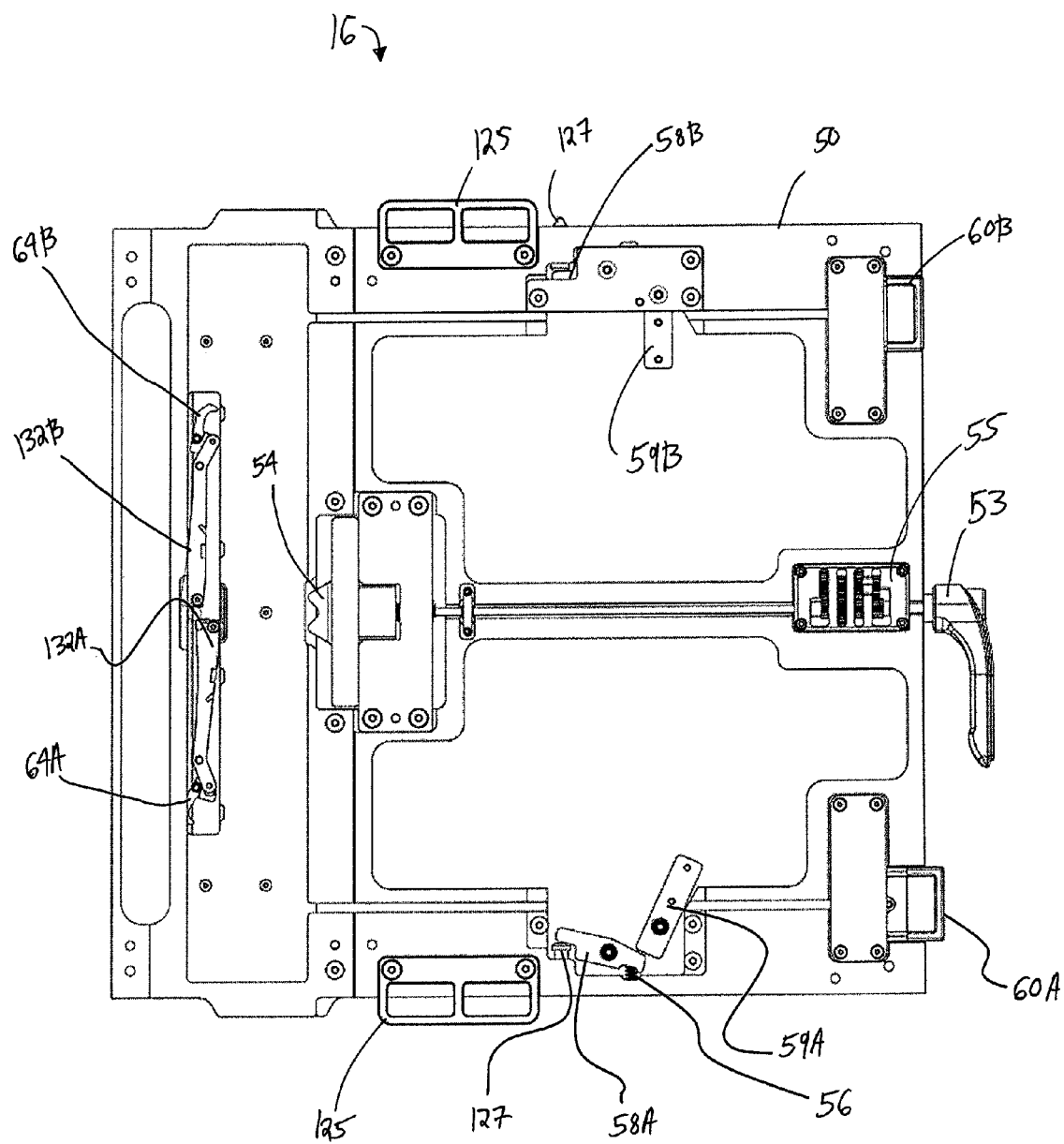
Figure 20C:
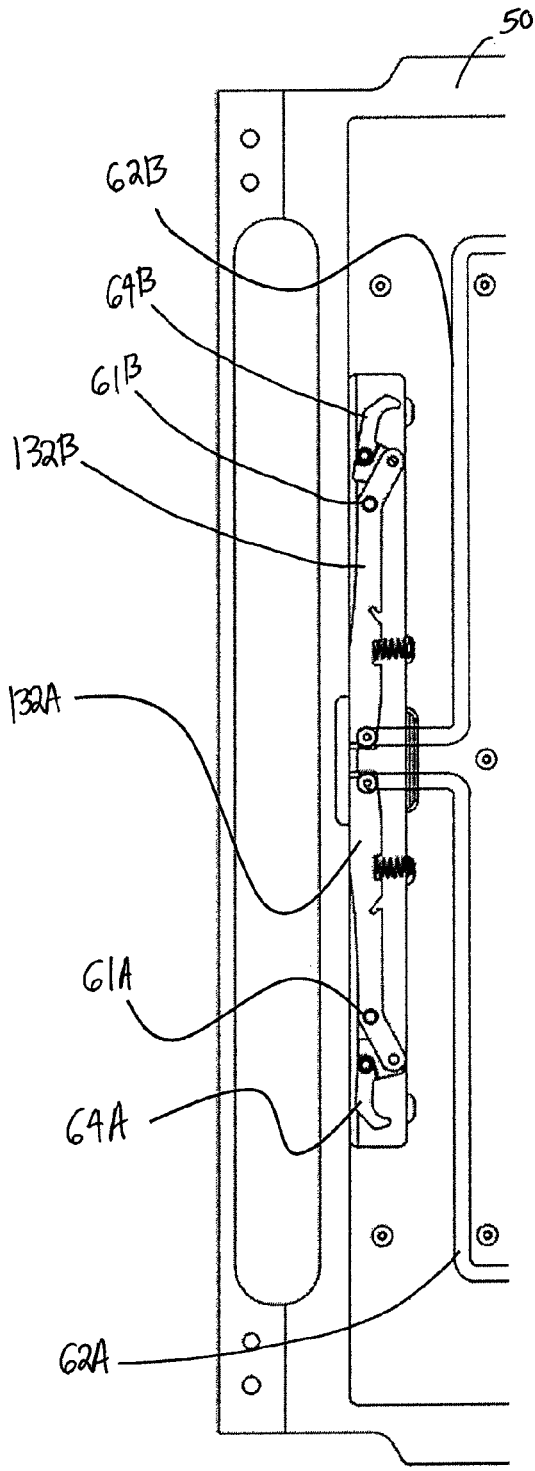
FIG. 20C is a partial exploded bottom view of the target modality assembly of FIG. 20A.
Figure 20D:
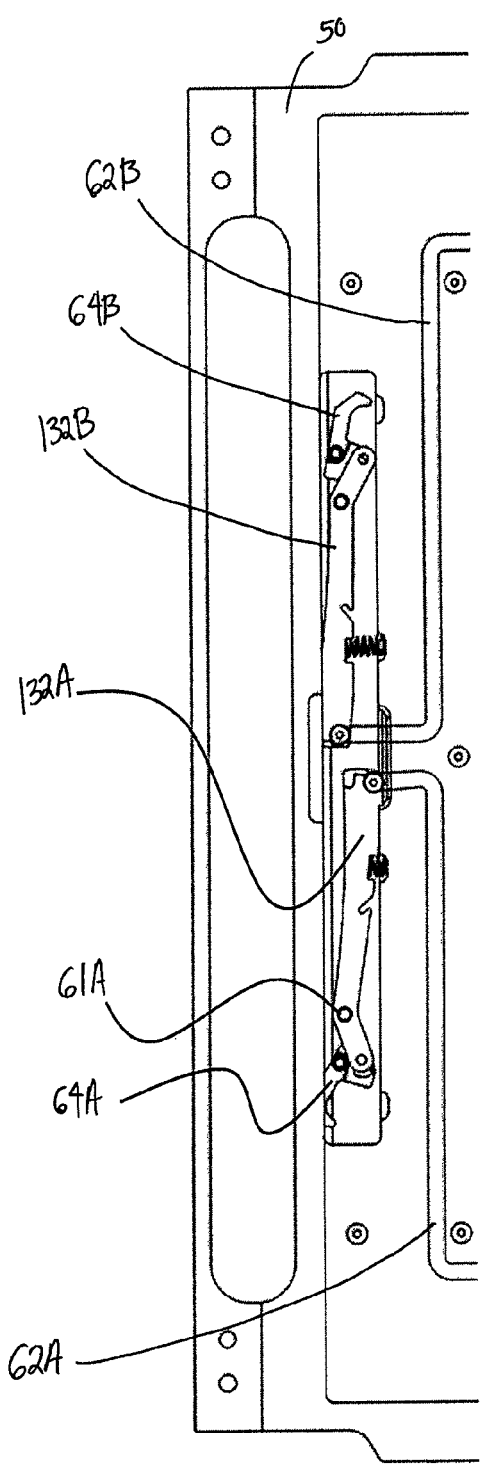
FIG. 20D is a partial exploded bottom view of the target modality assembly of FIG. 20B.
Figure 21:
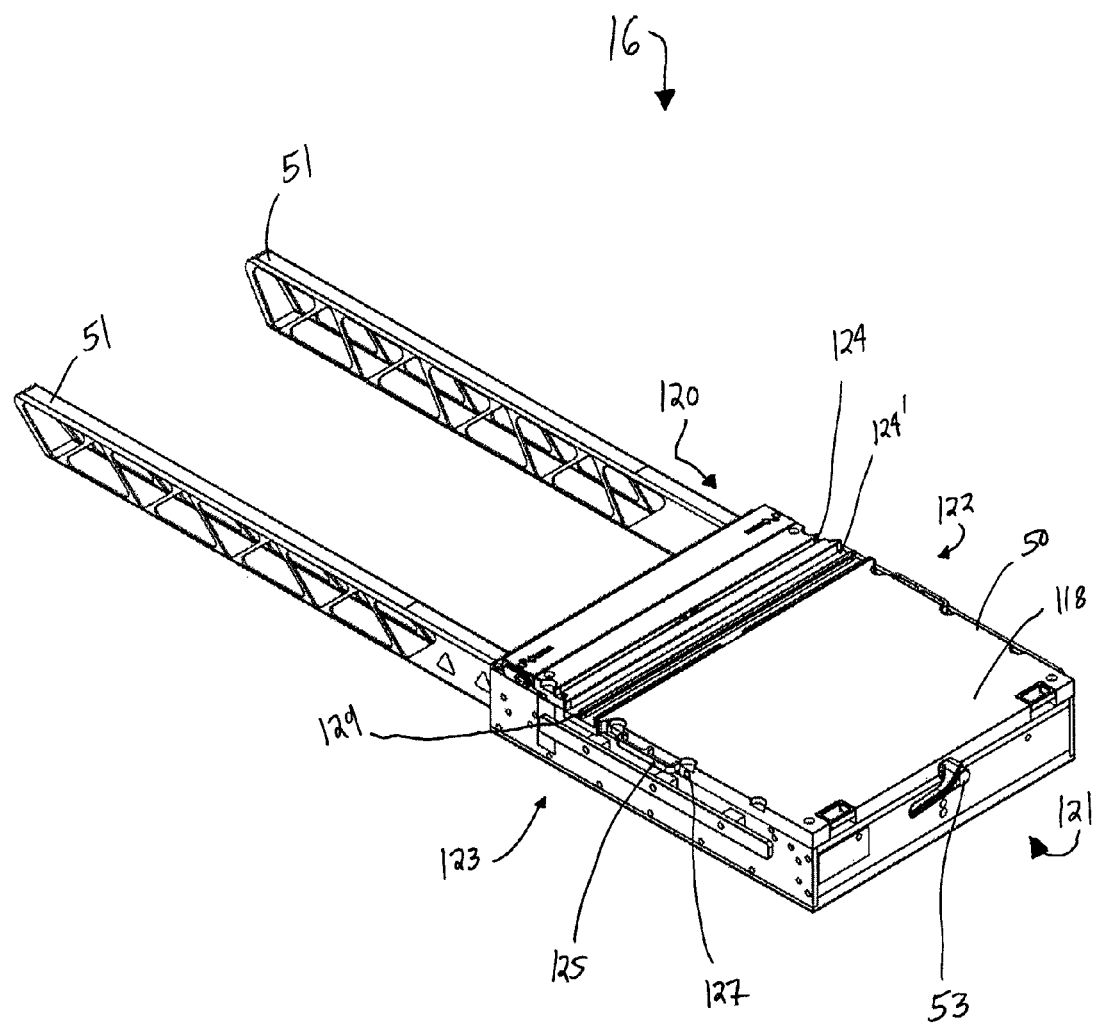
FIG. 21 is a partial top-side perspective view of the target modality assembly of FIG. 17.

As shown in FIGS. 20B-20D, after the interlock member 127 adjacent to assembly 12 is engaged/mated with and/or depressed by assembly 12, the engaged interlock member 127 rotates/moves its associated interlock transfer member 58A (FIG. 20B) to a position to allow the release cable pull member 59A to rotate (e.g., clockwise) when the safety latch release pull trigger 60A is utilized/pulled by a user, which thereby pulls the cable 62A (FIG. 20D) connected to safety latch 132A and puts the safety latch 132A (e.g., by rotating about hinge 61A) into the released position (FIGS. 20B and 20D) and allows the transfer assembly 14 to be moved to the trolley 12. A user would then ensure that the locking handle 53 was in the unlocked position (discussed further below), and then slide/move the transfer assembly 14 from the target modality assembly 16 to the trolley assembly 12 (e.g., by grasping and moving handles 45). The same released position/transferring functionality applies to interlock member 127 on side 122, and to its associated interlock transfer member 58B, release cable pull member 59B, safety latch release pull trigger 60B, hinge 61B and safety latch 132B (and safety latch reset member 64B), as shown in FIG. 20A.

In exemplary embodiments and during transfer of assembly 14 from assembly 16 to trolley 12, when the safety pin 34 of transfer assembly 14 is moved across/over released/depressed safety latch 132A (FIGS. 20B and 20D) and towards trolley 12, the safety pin 34 engages/hits a safety latch reset member 64A associated with safety latch 132A (e.g., a spring-loaded safety latch reset member 64A), which thereby resets safety latch 132A to the safety position as shown in FIG. 20A. The same reset functionality applies to safety latch 132B and safety latch reset member 64B.

As the transfer assembly 14 is being moved from the assembly 16 to the trolley 12, the safety pin 34 and extending members 35 and guide members 36 engage and/or are at least partially positioned within grooves 24 and/or 24' of trolley assembly 12 (e.g., FIG. 16). In exemplary embodiments, safety pin 34 would enter groove 24 and depress safety latch 32B of trolley 12 towards second end 21 until the safety pin 34 was securely and releasably positioned at least partially within recess 33. After safety pin 34 was positioned in recess 33 (and no longer positioned or travelling over latch 32B), the latch 32 is configured to automatically rise back up (e.g., safety latches 32B and 32A, and 132A/132B, are spring loaded) to the position as shown in FIG. 8. In other embodiments, safety pin 34 enters groove 24 and does not substantially depress safety latch 32B, but instead rides up safety latch 32B (or latches 32A, 132A, 132B) until it falls or moves into position in recess 33 (or recess 133).

After transfer assembly 14 has been securely and releasably mounted with respect to trolley assembly 12 (e.g., transfer assembly 14 has been positioned so that safety pin 34 is releasably positioned within recess 33, and/or extending members 35 and guide members 36 engage and/or are at least partially positioned within grooves 24 and/or 24'), the trolley assembly 12 with its releasably secured assembly 14 mounted thereon can be moved/transferred to other locations/positions (e.g., via wheels 13 of trolley 12) (FIGS. 1 and 11).

Figure 23:
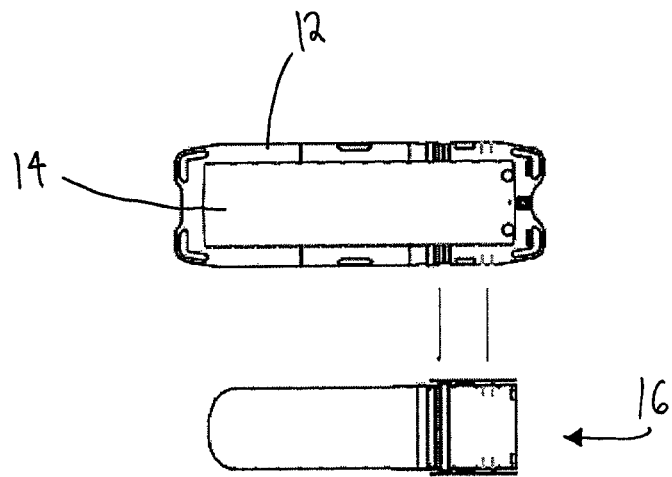
FIGS. 23-24 are top views of an exemplary trolley assembly, transfer assembly and target modality assembly according to the present disclosure.
Figure 24:
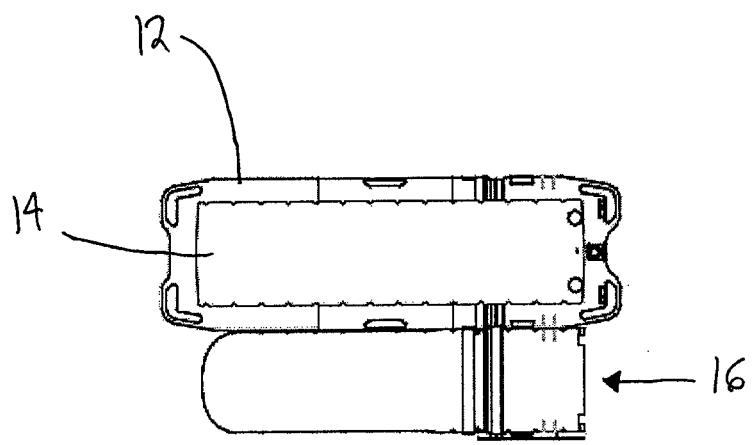

Thereafter and as shown in FIGS. 23-26, when it is desired to move the releasably secured transfer assembly 14 from the trolley 12 to target modality assembly 16 (or 16'), first a user can first position trolley assembly 12 adjacent to target modality assembly 16 as shown in FIGS. 23-24. Again, however, it is noted that mounted transfer assembly 14 can be loaded or unloaded from either side 22, 23 of trolley assembly 12. As noted, prior to or during placement of trolley assembly 12 adjacent to target modality assembly 16, a user can pull the appropriate fastener member trigger 225 on trolley assembly 12 to raise/lift the fastener member 25 (e.g., docking hook) upwards.

Once trolley assembly 12 is adjacent to target modality assembly 16 and positioned so that grooves 24, 24' substantially align with grooves 124, 124', the fastener member 25 releasably and securely engages/mates with securement member 125 (e.g., docking latch) of back panel 50. As similarly discussed above, when assembly 12 is adjacent to target modality assembly 16, the respective interlock member 27 of assembly 12 adjacent to target modality assembly 16 is engaged/mated with and/or depressed by assembly 16, and the respective interlock member 127 of assembly 16 adjacent to assembly 12 is engaged/mated with and/or depressed by assembly 12.

Figure 25:
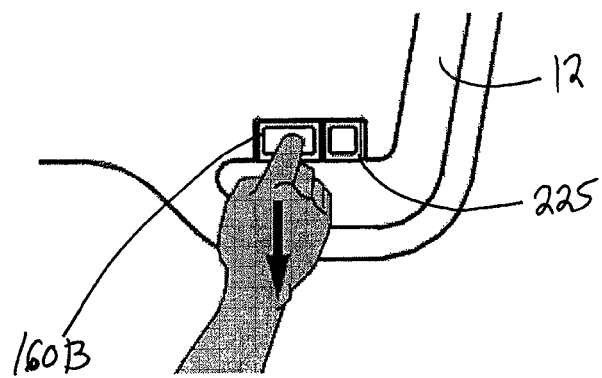
FIG. 25 is a partial top view of the trolley assembly of FIG. 23.
Figure 26:
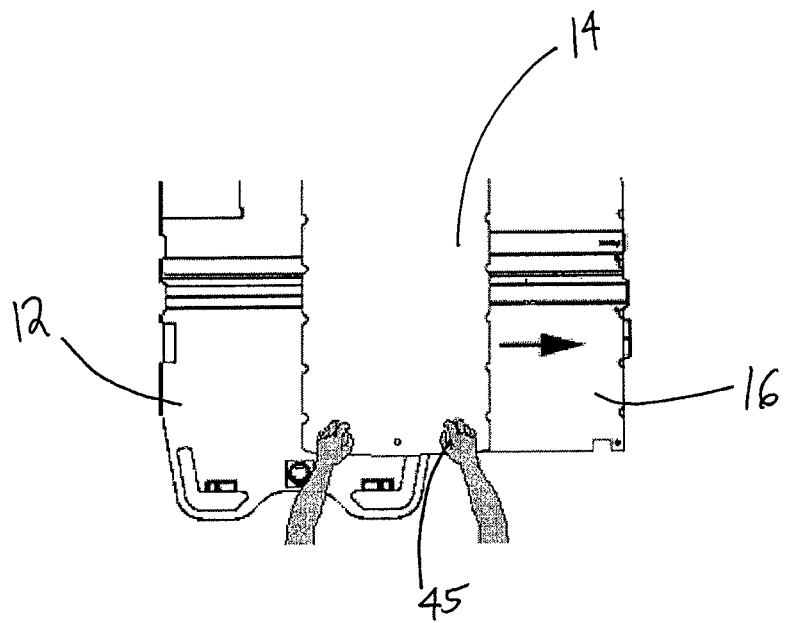
FIG. 26 is a partial top view of the trolley assembly, transfer assembly and target modality assembly of FIG. 23.

As shown in FIG. 24, after the trolley assembly 12 is adjacent to target modality assembly 16 (positioned so that grooves 24, 24' substantially align with grooves 124, 124'), and fastener member 25 is releasably and securely engaged/mated with securement member 125, and the interlock member 27 adjacent to treatment assembly 16 is engaged/mated with and/or depressed by assembly 16, and the interlock member 127 adjacent to assembly 12 is engaged/mated with and/or depressed by assembly 12, the user is now ready to proceed further with the process of moving assembly 14 from trolley 12 to assembly 16 (FIGS. 25-26).

Figure 10:
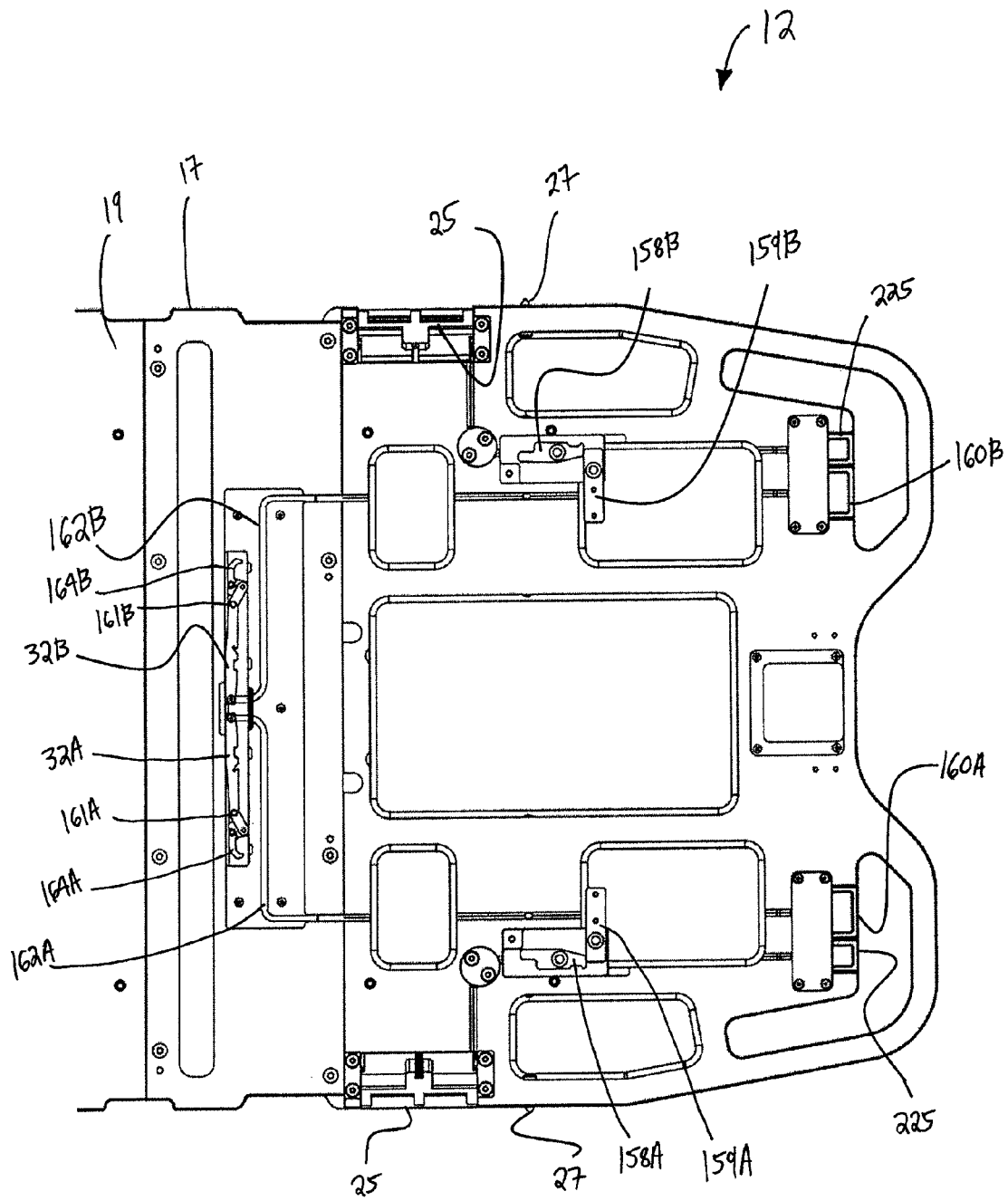
FIG. 10 is a partial bottom view of the trolley assembly of FIG. 5, with base member and column members removed from the trolley assembly for clarity.

However and as shown in FIG. 10, prior to the interlock member 27 adjacent to assembly 16 (FIG. 26) being engaged/mated with and/or depressed by assembly 16, the interlock member 27 will not be depressed/engaged. Because of this and as shown in FIG. 10, the interlock transfer member 158B associated with its respective interlock member 27 will be oriented/positioned to prevent its associated release cable pull member 159B from rotating (e.g., counter-clockwise in FIG. 10). Because the release cable pull member 159B cannot rotate in this position/orientation, the associated safety latch release pull trigger 160B cannot be pulled/activated/engaged, and its associated safety latch 32B will stay in place (e.g., will keep safety pin 34 in recess 33). The same safety functionality applies to interlock member 27 on side 23, and to its associated interlock transfer member 158A, release cable pull member 159A, safety latch release pull trigger 160A and safety latch 32A, as shown in FIG. 10.

As similarly described and disclosed in connection with FIGS. 20B-20D, after the interlock member 27 adjacent to assembly 16 is engaged/mated with and/or depressed by assembly 16, the engaged interlock member 27 rotates/moves its associated interlock transfer member 158B to a position to allow the release cable pull member 159B to rotate (e.g., counter-clockwise) when the safety latch release pull trigger 160B is utilized/pulled by a user, which thereby pulls the cable 162B connected to safety latch 32B and puts the safety latch 32B (e.g., by rotating about hinge 161B) into the released position and allows the transfer assembly 14 to be moved from the trolley 12. A user would then slide/move the transfer assembly 14 from the trolley 12 to the target modality assembly 16 (e.g., by grasping and moving handles 45—FIG. 26). The same released position/transferring functionality applies to interlock member 27 on side 23, and to its associated interlock transfer member 158A, release cable pull member 159A, safety latch release pull trigger 160A, hinge 161A and safety latch 32A (and safety latch reset member 164A), as shown in FIG. 10.

In exemplary embodiments and during transfer of assembly 14 from trolley 12 to assembly 16 (and as similarly discussed above), when the safety pin 34 of transfer assembly 14 is moved across/over released/depressed safety latch 32B and towards assembly 16, the safety pin 34 engages/hits a safety latch reset member 164B associated with safety latch 32B, which thereby resets safety latch 32B to the safety position as shown in FIG. 10. The same reset functionality applies to safety latch 32A and safety latch reset member 164A.

As the transfer assembly 14 is being moved from the trolley 12 to the assembly 16, the safety pin 34 and extending members 35 and guide members 36 engage and/or are at least partially positioned within grooves 124 and/or 124' of assembly 16 (e.g., FIG. 22). In exemplary embodiments, safety pin 34 would enter groove 124 and depress safety latch 132A of assembly 16 towards second end 121 until the safety pin 34 was securely and releasably positioned at least partially within recess 133. After safety pin 34 was positioned in recess 133 (and no longer positioned or travelling over latch 132A), the latch 132 is configured to automatically rise back up to the position as shown in FIG. 20A.

After transfer assembly 14 has been securely and releasably mounted with respect to target modality assembly 16 (e.g., transfer assembly 14 has been positioned so that safety pin is releasably positioned within recess 133, and/or extending members 35 and guide members 36 engage and/or are at least partially positioned within grooves 124 and/or 124'), the target modality assembly 16 with its releasably secured assembly 14 mounted thereon can be utilized for treatment/imaging purposes or the like.

Moreover and in exemplary embodiments, after transfer assembly 14 has been securely and releasably mounted with respect to target modality assembly 16 (e.g., transfer assembly 14 has been positioned so that safety pin 34 is releasably positioned within recess 133, and/or extending members 35 and guide members 36 engage and/or are at least partially positioned within grooves 124 and/or 124'), the locating member 38 is positioned/engaged relative to locking member 54 (FIGS. 18A-18C).

In certain embodiments and as shown in FIGS. 20A-20B, locking member 54 can be operatively associated with or mounted with respect to locking handle 53. Moreover, locking handle 53 and/or locking member 54 can be operatively associated with or mounted with respect to locking gearbox 55 (e.g., to amplify the movement and/or force of handle 53). In use, a user may utilize/rotate/move locking handle 53 to thereby move the locking member 54 towards the first end 120, which thereby pushes/engages the locating member 38 towards first end 120. In exemplary embodiments, the locating member 38 is moved towards first end 120 and is moved toward and/or engages/contacts the wall 129, and also urges/presses extending members 35 and/or guide members 36 in section 130 into engagement with wall member 147 (and/or also urges/presses extending members 35 and/or guide members 36 in section 131 into engagement with wall member 129), which thereby advantageously prevents transfer assembly 14 from rotating when releasably secured as such on treatment assembly 16.

In certain embodiments, when the transfer assembly 14 is moved to the target modality assembly 16, the locating member 38 engages with the locking member 54 and allows a user to accurately and repeatably locate and rigidly lock the transfer assembly 14 to the target modality assembly 16 in a releasable manner. In some embodiments, the locating member 38 and locking member 54 are configured to allow the user to accurately and repeatably locate and rigidly lock the transfer assembly 14 to the target modality assembly 16 to the level of sub-millimeter accuracy (e.g., which can be important for precise tumor targeting, etc.).

As noted above, to remove transfer assembly 14 from assembly 16, a user can un-secure the locking member 38 by turning/moving handle 53 (and therefore locking member 54) to the unlocked position.

It is noted that trolley assembly 12 may or may not include a locking member, locking handle and/or locking gearbox similar to locking member 54, locking handle 53 and/or locking gearbox 55 for securement/locking purposes of member 38 and/or of transfer assembly 14.

Figure 27:
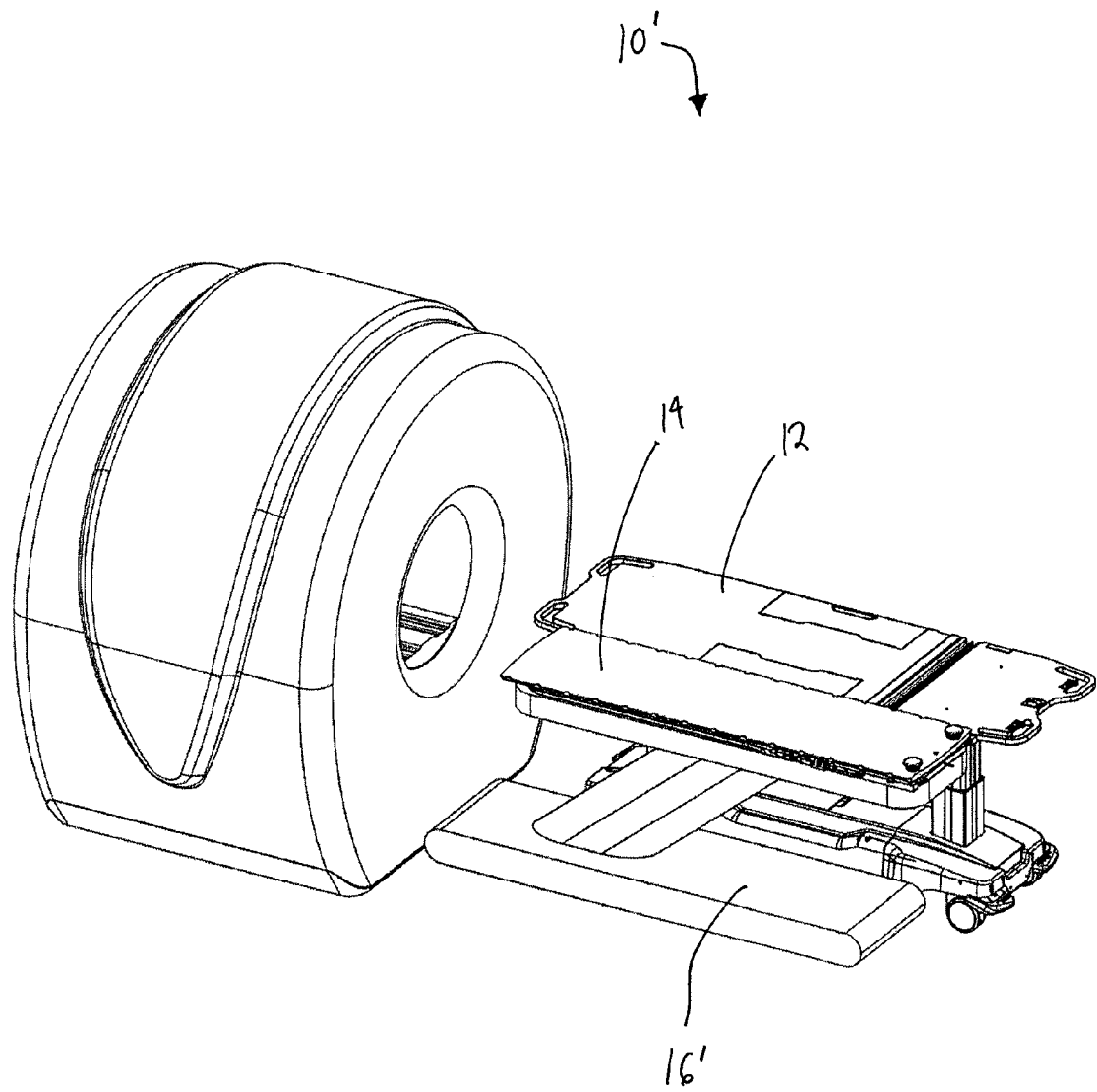
FIGS. 27-28 are side perspective views of another exemplary patient transport system according to the present disclosure.
Figure 28:
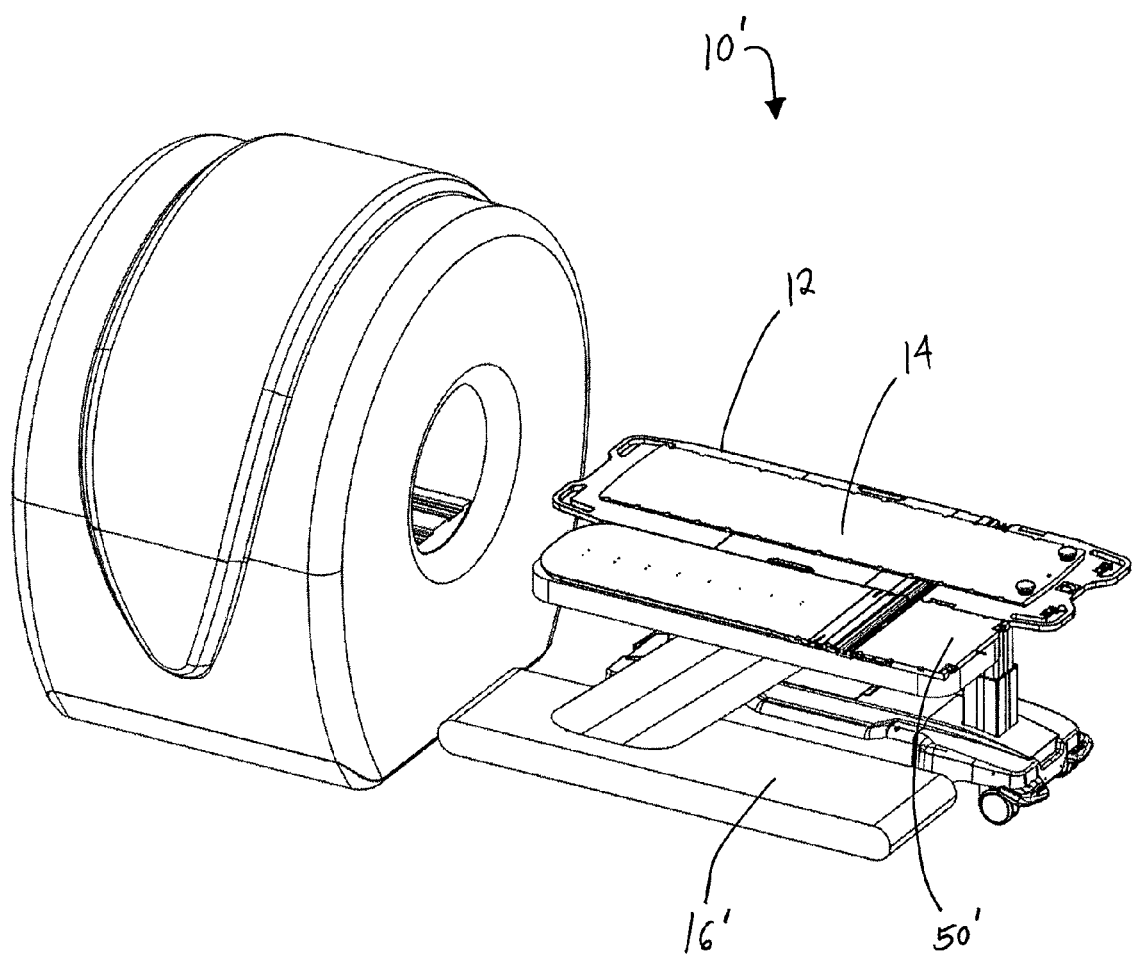

FIGS. 27-28 are side perspective views of another exemplary patient transport system 10' according to the present disclosure. More particularly, patient transport system 10' utilizes trolley assembly 12, transfer assembly 14 and/or target modality assembly 16' (e.g., diagnostic imaging target modality assembly 16') for patient transporting and/or imaging/treatment purposes. For example, assembly 16' can be an imaging target modality assembly 16', such as, without limitation, a CT or MRI imaging target modality assembly 16', although the present disclosure is not limited thereto. It is noted that assembly 16' includes back panel member 50', which can be similar to member 50 as disclosed and described above.

Whereas the disclosure has been described principally in connection with advantageous patient transport systems for hospital, treatment center and/or commercial uses/purposes, such description has been utilized only for purposes of disclosure and is not intended as limiting the disclosure. To the contrary, it is to be recognized that the disclosed patient transport systems are capable of use for other applications and/or uses/purposes.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A patient transport system comprising:
   a target modality assembly;
   a patient transfer assembly, the transfer assembly configured and dimensioned to be releasably mounted with respect to the target modality assembly;
   wherein when the transfer assembly is moved to the target modality assembly, the transfer assembly is moved to a predetermined stop position on the target modality assembly to allow a user to safely, accurately and repeatably releasably mount the transfer assembly to the target modality assembly;
a trolley assembly, the trolley assembly having a safety member catch;
wherein the transfer assembly is configured and dimensioned to be releasably mounted with respect to the trolley assembly;
and wherein when the transfer assembly is moved from the target modality assembly to the trolley assembly, a safety member of the transfer assembly engages with the safety member catch of the trolley assembly to allow a user to safely, accurately and repeatably releasably mount the transfer assembly to the trolley assembly; and
wherein the transfer assembly is configured to be laterally moved from either lateral side of the target modality assembly across either lateral side of the trolley assembly to a predetermined stop position on the trolley assembly to releasably mount the transfer assembly to the trolley assembly.

2. The patient transport system of claim 1, wherein the target modality assembly includes a safety member catch; and wherein when the transfer assembly is moved to the target modality assembly, a safety member of the transfer assembly engages with the safety member catch of the target modality assembly to allow a user to safely, accurately and repeatably releasably mount the transfer assembly to the target modality assembly.

3. The patient transport system of claim 2, wherein when the safety member is engaged with the safety member catch of the target modality assembly and the safety member catch is in a safety position, the transfer assembly is prevented from moving laterally relative to the target modality assembly.

4. The patient transport system of claim 2, wherein when the transfer assembly is releasably mounted to the target modality assembly, the safety member catch and the safety member are positioned outside of the treatment or imaging area of the target modality assembly.

5. The patient transport system of claim 2, wherein the safety member catch of the target modality assembly is defined by a first safety latching member and a second safety latching member when the first and second safety latching members are in a safety position; wherein a top side of the target modality assembly includes a first groove; and wherein at least a portion of the first and second safety latching members are positioned within the first groove when the first and second safety latching members are in the safety position; wherein the top side of the target modality assembly includes a second groove; wherein the transfer assembly includes a guide member, the guide member extending from a bottom side of the transfer assembly; wherein at least a portion of the guide member is positioned within the second groove when the transfer assembly is releasably mounted to the target modality assembly; and wherein the guide member is configured and dimensioned to engage the second groove and prevent the transfer assembly from being lifted vertically or upwardly off of the target modality assembly when the transfer assembly is releasably mounted to the target modality assembly.

6. The patient transport system of claim 1, wherein when the safety member is engaged with the safety member catch of the trolley assembly and the safety member catch is in a safety position, the transfer assembly is prevented from moving laterally relative to the trolley assembly.

7. The patient transport system of claim 1, wherein the target modality assembly further includes a locking member and the transfer assembly includes a locating member; wherein when the transfer assembly is moved to the target modality assembly, the locating member engages with the locking member and allows a user to accurately and repeatably locate and rigidly lock in one location the transfer assembly to the target modality assembly in a releasable manner; wherein a top side of the target modality assembly includes a groove; wherein the transfer assembly includes an extending member, the extending member extending from a bottom side of the transfer assembly; wherein at least a portion of the extending member is positioned within the groove when the transfer assembly is releasably mounted to the target modality assembly; and wherein when the transfer assembly is releasably locked to the target modality assembly, the locking member urges the extending member into releasable locking contact with a wall of the groove to rigidly lock the transfer assembly to the target modality assembly in a releasable manner.

8. The patient transport system of claim 7, wherein the locating member and locking member are configured to allow the user to accurately and repeatably locate and rigidly lock in one location the transfer assembly to the target modality assembly to the level of sub-millimeter accuracy.

9. The patient transport system of claim 1, wherein a top side of the target modality assembly includes an extending member, the extending member extending from the top side of the target modality assembly; wherein a bottom side of the transfer assembly includes a groove; and wherein at least a portion of the extending member is positioned within the groove when the transfer assembly is releasably mounted to the target modality assembly.

10. A patient transport system comprising:
a target modality assembly;
a patient transfer assembly, the transfer assembly configured and dimensioned to be releasably mounted with respect to the target modality assembly;
wherein when the transfer assembly is moved to the target modality assembly, the transfer assembly is moved to a predetermined stop position on the target modality assembly to allow a user to safely, accurately and repeatably releasably mount the transfer assembly to the target modality assembly;
wherein a top side of the target modality assembly includes an extending member, the extending member extending from the top side of the target modality assembly;
wherein a bottom side of the transfer assembly includes a groove; and
wherein at least a portion of the extending member is positioned within the groove when the transfer assembly is releasably mounted to the target modality assembly.

11. A patient transport system comprising:
a target modality assembly, the target modality assembly having an interlock member;
a trolley assembly, the trolley assembly having an interlock member;
a patient transfer assembly, the transfer assembly configured and dimensioned to be releasably mounted with respect to the trolley assembly or to the target modality assembly;
wherein when the transfer assembly is releasably mounted with respect to the trolley assembly, the engagement of the interlock member of the trolley assembly with the target modality assembly allows the transfer assembly to be released from the trolley assembly and moved to the target modality assembly;

wherein the target modality assembly includes a safety member catch and the trolley assembly includes a safety member catch;

wherein when the transfer assembly is moved to the target modality assembly, a safety member of the transfer assembly engages with the safety member catch of the target modality assembly to allow a user to safely, accurately and repeatably releasably mount the transfer assembly to the target modality assembly;

wherein when the transfer assembly is releasably mounted with respect to the target modality assembly, the engagement of the interlock member of the target modality assembly with the trolley assembly allows the transfer assembly to be released from the target modality assembly and moved to the trolley assembly; and wherein when the transfer assembly is moved from the target modality assembly to the trolley assembly, the safety member of the transfer assembly engages with the safety member catch of the trolley assembly to allow a user to safely, accurately and repeatably releasably mount the transfer assembly to the trolley assembly.

12. The patient transport system of claim 11, wherein the transfer assembly is configured to be laterally moved from either lateral side of the trolley assembly across either lateral side of the target modality assembly to a predetermined stop position on the target modality assembly to releasably mount the transfer assembly to the target modality assembly.

13. The patient transport system of claim 12, wherein a top side of the target modality assembly includes an extending member, the extending member extending from the top side of the target modality assembly; wherein a bottom side of the transfer assembly includes a groove; and wherein at least a portion of the extending member is positioned within the groove when the transfer assembly is releasably mounted to the target modality assembly.

14. The patient transport system of claim 11, wherein when the transfer assembly is releasably mounted with respect to the target modality assembly, the engagement of the interlock member of the target modality assembly with the trolley assembly allows the transfer assembly to be released from the target modality assembly and moved to the trolley assembly.

15. The patient transport system of claim 14, wherein the transfer assembly is configured to be laterally moved from either lateral side of the target modality assembly across either lateral side of the trolley assembly to a predetermined stop position on the trolley assembly to releasably mount the transfer assembly to the trolley assembly.

16. The patient transport system of claim 11, wherein when the safety member is engaged with the safety member catch of the target modality assembly and the safety member catch is in a safety position, the transfer assembly is prevented from moving laterally relative to the target modality assembly; and wherein when the safety member is engaged with the safety member catch of the trolley assembly and the safety member catch is in a safety position, the transfer assembly is prevented from moving laterally relative to the trolley assembly.

17. The patient transport system of claim 11, wherein the safety member catch of the target modality assembly is defined by a first safety latching member and a second safety latching member when the first and second safety latching members are in a safety position; wherein a top side of the target modality assembly includes a first groove; and wherein at least a portion of the first and second safety latching members are positioned within the first groove when the first and second safety latching members are in a safety position.

18. The patient transport system of claim 17, wherein the top side of the target modality assembly includes a second groove; wherein the transfer assembly includes a guide member, the guide member extending from a bottom side of the transfer assembly; wherein at least a portion of the guide member is positioned within the second groove when the transfer assembly is releasably mounted to the target modality assembly; and wherein the guide member is configured and dimensioned to engage the second groove and prevent the transfer assembly from being lifted vertically or upwardly off of the target modality assembly when the transfer assembly is releasably mounted to the target modality assembly.

19. The patient transport system of claim 17, wherein when the interlock member of the trolley assembly is engaged with the target modality assembly, the engaged interlock member moves an interlock transfer member to a position to allow a release cable pull member to rotate when a safety latch release pull trigger is utilized by a user, which thereby pulls a cable connected to the first safety latching member and puts the first safety latching member into a released position that allows the transfer assembly to be moved to the target modality assembly; and wherein when the transfer assembly is moved to the target modality assembly, the safety member of the transfer assembly is configured to depress a safety latch reset member of the first safety latching member, which thereby resets the first safety latching member to the safety position after the transfer assembly is moved to the target modality assembly.

20. The patient transport system of claim 11, wherein the target modality assembly further includes a locking member and the transfer assembly includes a locating member; wherein when the transfer assembly is moved to the target modality assembly, the locating member engages with the locking member and allows a user to accurately and repeatably locate and rigidly lock in one location the transfer assembly to the target modality assembly in a releasable manner; wherein a top side of the target modality assembly includes a groove; wherein the transfer assembly includes an extending member, the extending member extending from a bottom side of the transfer assembly; wherein at least a portion of the extending member is positioned within the groove when the transfer assembly is releasably mounted to the target modality assembly; and wherein when the transfer assembly is releasably locked to the target modality assembly, the locking member urges the extending member into releasable locking contact with a wall of the groove to rigidly lock the transfer assembly to the target modality assembly in a releasable manner.

21. The patient transport system of claim 20, wherein the locating member and locking member are configured to allow the user to accurately and repeatably locate and rigidly lock in one location the transfer assembly to the target modality assembly to the level of sub-millimeter accuracy.

* * * * *